(12) United States Patent
Hatch et al.

(10) Patent No.: US 11,627,212 B2
(45) Date of Patent: Apr. 11, 2023

(54) CLAMP TO ATTACH ELECTRONIC DEVICE HOLDER TO BED RAIL

(71) Applicant: Hatchmed Corporation, Seattle, WA (US)

(72) Inventors: Brian Hatch, Seattle, WA (US); Kyrylo Keydanskyy, Seattle, WA (US)

(73) Assignee: HATCHMED CORPORATION, Seattle, WA (US)

( * ) Notice: Subject to any disclaimer, the term of this patent is extended or adjusted under 35 U.S.C. 154(b) by 194 days.

(21) Appl. No.: 17/087,308

(22) Filed: Nov. 2, 2020

(65) Prior Publication Data
US 2021/0051222 A1    Feb. 18, 2021

Related U.S. Application Data

(63) Continuation-in-part of application No. 16/827,554, filed on Mar. 23, 2020, now Pat. No. 10,863,012.
(Continued)

(51) Int. Cl.
*H01R 13/46* (2006.01)
*H01R 13/62* (2006.01)
(Continued)

(52) U.S. Cl.
CPC ............ *H04M 1/04* (2013.01); *A61B 5/7445* (2013.01); *G06F 1/1632* (2013.01);
(Continued)

(58) Field of Classification Search
CPC ............... H04M 1/04; H04M 1/72541; H04M 1/72424; A61B 5/7445; A61B 5/74;
(Continued)

(56) References Cited

U.S. PATENT DOCUMENTS 3,316,044 A    4/1967 Carbary
3,942,751 A    3/1976 Fay
(Continued)

FOREIGN PATENT DOCUMENTS

CN    201479176    5/2010
CN    202949471    5/2013
(Continued)

OTHER PUBLICATIONS

"2014 Manufacturers' Excellence Awards Finalists", Crestron Pyng™, Available Online at: http://cedia.net/programs/awards/winners/2014-manufacturers%27-excellence-awards-fina . . . , Accessed from Internet on Jul. 29, 2019, 15 pages.
(Continued)

*Primary Examiner* — Angel R Estrada
(74) *Attorney, Agent, or Firm* — Kilpatrick Townsend & Stockton LLP

(57) ABSTRACT

A personal electronic device holder with a clamp is described. The clamp including a body having a U-shape, a first surface, and a second surface. The first surface and the second surface positionable to selectively clamp against a side rail of health care facility equipment. The holder also includes a structure for retaining and powering or providing data and power to a personal electronic device at the end of a positionable arm connected to the clamp.

28 Claims, 19 Drawing Sheets

Related U.S. Application Data which is a continuation of application No. 16/035,283, filed on Jul. 13, 2018, now Pat. No. 10,601,971.

(60) Provisional application No. 62/567,670, filed on Oct. 3, 2017.

(51) Int. Cl.

| | | |
|---|---|---|
| *H04M 1/04* | (2006.01) | |
| *A61B 5/00* | (2006.01) | |
| *G08B 25/01* | (2006.01) | |
| *G06F 1/16* | (2006.01) | |
| *G08B 25/08* | (2006.01) | |
| *A61G 7/05* | (2006.01) | |
| *H04M 1/72424* | (2021.01) | |

(52) U.S. Cl.
CPC ........... *G08B 25/016* (2013.01); *G08B 25/08* (2013.01); *A61G 7/0524* (2016.11); *A61G 2203/20* (2013.01); *H01R 13/6205* (2013.01); *H01R 2201/12* (2013.01); *H04M 1/72424* (2021.01)

(58) Field of Classification Search
CPC ..... G06F 1/1632; G06F 1/633; G08B 25/016; G08B 25/08; A61G 7/0524; A61G 2203/20; H01R 13/6205; H01R 2201/12; H01R 13/46; H02G 3/08; H02G 3/081
USPC ... 174/59, 480, 482, 500, 501, 503, 50, 520, 174/58, 61; 220/3.2, 3.3, 4.01; 248/906, 248/200; 5/503.1, 658
See application file for complete search history.

(56) References Cited

U.S. PATENT DOCUMENTS

| | | | |
|---|---|---|---|
| 4,680,790 A | 7/1987 | Packard et al. | |
| 5,273,354 A | 12/1993 | Herrmann et al. | |
| 5,365,689 A * | 11/1994 | Holliman | A01K 97/10 248/530 |
| 5,701,991 A | 12/1997 | Helmetsie | |
| 5,802,636 A | 9/1998 | Corbin et al. | |
| 5,867,821 A | 2/1999 | Ballantyne et al. | |
| 6,206,464 B1 | 3/2001 | Santa Rosa et al. | |
| 6,339,410 B1 | 1/2002 | Milner et al. | |
| 6,407,335 B1 | 6/2002 | Franklin-lees et al. | |
| 6,486,792 B1 | 11/2002 | Moster et al. | |
| 6,622,980 B2 | 9/2003 | Boucher et al. | |
| 7,349,203 B2 | 3/2008 | Jobs et al. | |
| 7,377,472 B2 * | 5/2008 | Brown | F16L 3/10 248/74.1 |
| 7,458,555 B2 | 12/2008 | Mastropaolo et al. | |
| 7,730,565 B1 | 6/2010 | Masson | |
| 7,778,848 B1 | 8/2010 | Reeves | |
| 7,821,782 B2 | 10/2010 | Doherty et al. | |
| 7,861,985 B2 | 1/2011 | Galvin | |
| 7,967,137 B2 | 6/2011 | Fulbrook et al. | |
| 7,971,289 B2 | 7/2011 | Payne et al. | |
| 7,992,833 B1 * | 8/2011 | Goodman | A47G 25/0614 248/307 |
| 8,011,629 B2 | 9/2011 | Herskovic | |
| 8,020,829 B1 | 9/2011 | Tamayori | |
| 8,053,670 B2 | 11/2011 | Lin et al. | |
| 8,461,968 B2 | 6/2013 | Ball et al. | |
| 8,485,404 B2 | 7/2013 | Monaco et al. | |
| 8,499,384 B2 | 8/2013 | Zerhusen | |
| D692,439 S | 10/2013 | Muhlenberg | |
| 8,602,662 B1 | 12/2013 | Mans | |
| 8,607,388 B1 | 12/2013 | Flanagan et al. | |
| 8,650,682 B2 | 2/2014 | Herman | |
| 8,661,583 B2 | 3/2014 | Chinn et al. | |
| 8,727,804 B2 | 5/2014 | McNeely et al. | |
| 8,763,802 B2 | 7/2014 | Ellis-Brown | |
| 8,789,802 B2 | 7/2014 | Springer et al. | |
| 8,794,766 B2 | 8/2014 | Listou | |
| 8,867,198 B2 | 10/2014 | Steele | |
| 8,917,496 B2 | 12/2014 | Richardson et al. | |
| 8,944,826 B1 | 2/2015 | Wilkolaski et al. | |
| 8,994,776 B2 | 3/2015 | Sutherland et al. | |
| 9,038,971 B1 | 5/2015 | Guthrie | |
| 9,147,965 B2 | 9/2015 | Lee | |
| 9,243,839 B2 | 1/2016 | Kim et al. | |
| 9,286,441 B2 | 3/2016 | Zerhusen et al. | |
| 9,375,374 B2 | 6/2016 | Herman et al. | |
| 9,444,237 B2 | 9/2016 | Frojo | |
| 9,463,126 B2 | 10/2016 | Zerhusen et al. | |
| D773,465 S | 12/2016 | Palmer et al. | |
| 9,573,686 B2 | 2/2017 | Barth | |
| 9,643,767 B2 | 5/2017 | Ziemba | |
| 9,680,518 B2 | 6/2017 | Wojcik et al. | |
| 9,743,357 B2 | 8/2017 | Tabe | |
| 9,824,815 B2 | 11/2017 | Leabman et al. | |
| 10,013,868 B2 | 7/2018 | Cox et al. | |
| 10,028,875 B2 | 7/2018 | Hatch | |
| 10,175,723 B2 | 1/2019 | Weldon | |
| 10,601,971 B2 | 3/2020 | Hatch et al. | |
| 10,863,012 B2 | 12/2020 | Hatch et al. | |
| 2001/0022719 A1 | 9/2001 | Armitage et al. | |
| 2004/0174107 A1 | 9/2004 | O'Halloran | |
| 2005/0062380 A1 | 3/2005 | Park et al. | |
| 2009/0255292 A1 | 10/2009 | Benz | |
| 2010/0064721 A1 | 3/2010 | Shin et al. | |
| 2010/0132122 A1 | 6/2010 | Hollingshead | |
| 2011/0210833 A1 | 9/2011 | McNeely et al. | |
| 2011/0214234 A1 | 9/2011 | Herman | |
| 2011/0290807 A1 | 12/2011 | Calvillo et al. | |
| 2012/0026684 A1 | 2/2012 | Matthews | |
| 2012/0215360 A1 | 8/2012 | Zerhusen et al. | |
| 2013/0093388 A1 | 4/2013 | Partovi | |
| 2013/0314866 A1 | 11/2013 | Millman | |
| 2015/0024611 A1 | 1/2015 | Wilkolaski et al. | |
| 2015/0351530 A1 | 12/2015 | Udagawa et al. | |
| 2016/0008197 A1 | 1/2016 | Zerhusen et al. | |
| 2016/0047594 A1 | 2/2016 | Choo et al. | |
| 2016/0128468 A1 | 5/2016 | Lafleche et al. | |
| 2016/0183393 A1 | 6/2016 | Groom et al. | |
| 2016/0190838 A1 | 6/2016 | Webb | |
| 2016/0228091 A1 | 8/2016 | Chiang et al. | |
| 2016/0324701 A1 | 11/2016 | Cambridge et al. | |
| 2017/0035295 A1 | 2/2017 | Collins, Jr. et al. | |
| 2017/0052581 A1 | 2/2017 | Enzinna | |
| 2018/0168900 A1 | 6/2018 | McNeely et al. | |

FOREIGN PATENT DOCUMENTS

| | | |
|---|---|---|
| EP | 2575263 | 4/2013 |
| KR | 20130004443 | 7/2013 |
| KR | 20170035851 | 3/2017 |
| WO | 2016155691 | 12/2016 |
| WO | 2016196403 | 12/2016 |
| WO | 2017131796 | 8/2017 |

OTHER PUBLICATIONS

"Announcing New Savant Home Automation Partners: Nest and iPort", INC, Available Online at: https://inctech.net/savant-announces-new-home-automation-partners/, Sep. 27, 2016, 2 pages.

"Camera SnakeClamp", Snake Clamp, Available on Internet at: https://web.archive.org/web/20121220014228/https://snakeclamp.com/Category/camera-snakeclamp-withflexible-gooseneck-arm#.WeENSuT2Z9A, Dec. 12, 2012, 3 pages.

Google Search, "iport OR OR OR Dana Innovations Surface Mount with Buttons• OR Launch Port with Buttons•", Available Online at: https://www.google.com/search?q=iport+OR+OR+OR+"dana+innovations"+"surface+mount+with+buttons•+OR+"launch+port+with+buttons•&rlz . . . , Accessed from Internet on Jul. 29, 2019, 2 pages.

"IPort® Announces the xPRESSTM Audio Keypad for Sonos®: Direct WiFi Control for Any Sonos Device", Available Online at: https://www.prnewswire.com/news-releases/iport-announces-the-

(56) References Cited

OTHER PUBLICATIONS xpress-audio-keypad-for-sonos-direct-wifi-control-for-any-sonos-device-300320239.h . . . , Aug. 30, 2016, 3 pages.

"Medical-Grade Tablet Cases Beat Pathogens", Maximise Technology, Available online at: https://www.maximisetechnology.com.au/medical-grade-device-cases-beat-pathogens-for-health-care/, 2019, 4 pages.

"Quality Gaming and Multimedia Accessories", CTA®, [online] ctadigital.com, Available Online at: http://web.archive,org/web/20160424204832/http://www.ctadigital.com:80/, Apr. 24, 2016, 5 pages.

RAM® Torque 3/4™-1" Diameter Handlebar/Rail are with 1", Ball Medium Arm and X-Grip® Mounts,, Available Online at: https://web.archive.org/web/20160616011725/http:www.rammount.com/part RAM-B-408-75-1-UN7U, Jun. 6, 2016, 9 pages.

"REGO Patient Interaction System", Curbell Medical, Online Available at: https://hellorego.com/, 8 pages.

"Roomie Remote Launches 3.0 App for Home Theater and Home Automation at a Fraction of the Cost of Traditional Touch Panel Systems", Available Online at: https://dialog.proquest.com/professional/printviewfile?accountid=157769, Sep. 30, 2014, 2 pages.

"Savant Home Automation Works with Nest and iPort, Integrates Deeper with Sonos, PureLink", Available Online at: https://www.cepro.com/article/savant_home_automation_works_with_nest_iport_integrates_deeper_with_sonos, Sep. 27, 2016, 2 pages.

"SVI Trade Awards 2017—The Winners!", Available Online at: https://wws.v.svimag.com/news/svi_trade_awards_2017_the_winners, Apr. 27, 2017, 5 pages.

U.S. Appl. No. 15/705,105, "Non Final Office Action", dated Nov. 14, 2017, 6 pages.

U.S. Appl. No. 15/705,105, "Notice of Allowance", dated Mar. 27, 2018, 5 pages.

U.S. Appl. No. 16/035,283, "Notice of Allowance", dated Jan. 17, 2020, 9 pages.

U.S. Appl. No. 16/827,554, "Non-Final Office Action", dated Jun. 12, 2020, 7 pages.

U.S. Appl. No. 16/827,554, "Notice of Allowance", dated Aug. 5, 2020, 8 pages.

* cited by examiner

CLAMP TO ATTACH ELECTRONIC DEVICE HOLDER TO BED RAIL

CROSS-REFERENCES TO RELATED APPLICATIONS

This application is a continuation-in-part of U.S. patent application Ser. No. 16/827,554, filed Mar. 23, 2020, and now granted as U.S. Pat. No. 10,863,012, which application is a continuation of U.S. patent application Ser. No. 16/035,283, filed Jul. 13, 2018, and now granted as U.S. Pat. No. 10,601,971, which application claims the benefit of U.S. Provisional Application No. 62/567,670, filed Oct. 3, 2017, the entire contents of each of which are hereby incorporated for all purposes in their entirety.

BACKGROUND OF THE INVENTION

Portable electronic devices (PEDs) (e.g., digital tablets, smart phones, and other electronic devices) are becoming more popular and prevalent in modern day lifestyles. Hospitals are experiencing increased usage of PEDs, either by patients and/or by hospital personnel. PEDs are being used in hospitals for communication, education, video conferencing with a patient who is in a hospital bed, and entertainment of the patient.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments herein are directed to portable electronic device (PED) related assemblies that are employable in a health care facility and can support the use of a PED or other electronic device on a wall of the health care facility to provide access to data and receive inputs and/or signals from users. In some embodiments, a PED related assembly includes one or more communication, data, and/or power cable assemblies that can be readily disconnected interchange, remove, or otherwise interact with the device. In some embodiments, a PED related assembly includes a PED holder with an output connector that is connectable to an input port of a PED held in the PED holder. As a result, a PED can be supplied power and/or data via a connection that enables use of the PED.

One general aspect includes a portable electronic device (PED) holder assembly for use in a healthcare facility, including: a device for connecting to a rail of health care facility equipment. The portable electronic device holder also includes a body having a u-shape including a base member with a first extension and a second extension extending perpendicularly from opposite ends of the base member. The portable electronic device holder also includes a first surface for positioning against a first side of the rail of the health care facility equipment, the first surface coupled to the first extension and including a concave surface. The portable electronic device holder also includes a second surface coupled to the second extension and for positioning against a second side of the rail, opposite the first side, when the device is installed on the rail, the first surface or second surface positionable along a movement axis extending from the first extension to the second extension in (1) an open position where the first surface and second surface are released to permit installation of the device on the rail and a (2) closed position where the first surface and second surface are positioned against the first side and the second side of the rail. The portable electronic device holder is adapted to hold a PED. The portable electronic device holder also includes a positionable arm coupled to the device at the base between the first surface and the second surface and perpendicular to the movement axis.

Implementations may include one or more of the following features. The PED holder assembly where the PED holder includes: one or more interfaces adapted for connection to a power and data cable of a health care facility, the one or more interfaces disposed in the PED holder. The PED holder assembly may also include an assistance request button associated with requesting assistance in the health care facility, the assistance request button disposed in the PED holder or the power and data cable, where a first interface of the one or more interfaces is operatively coupled with the PED such that power received from the power and data cable is provided from the first interface to the PED, and a second interface of one of the one or more interfaces is operatively coupled with a communication system of the health care facility such that an assistance request signal is provided from the second interface to the communication system via the power and data cable. The PED holder assembly where the second interface includes a releasable connector. The PED holder assembly where the first surface is coupled to the first extension via an actuation member, the actuation member coupled to the first surface to enable rotation of the first surface through a limited range of rotation. The limited range of rotation may be up to one hundred and eighty degrees. The PED holder assembly where the positionable arm includes a plurality of clamps arranged along a length thereof to support a power or data cable connected to a system of the healthcare facility. The PED holder assembly where the body includes a power converter configured to receive power input from a power cable of a health care facility and output a power output at a different voltage from a voltage of the power input. The PED holder assembly where the power converter receives the power input at twelve volts and outputs the power output at five volts. The PED holder assembly where the device includes a power outlet connected to a power supply of the healthcare facility for providing power to an electronic device. The PED holder assembly where the device includes an actuation device that changes a distance between the first surface and the second surface between the open position and the closed position and apply a force against the rail of the health care facility equipment. The PED holder assembly where each of the second surface and first surface include a planar surface to enable the device to secure against a planar surface of health care facility equipment. The PED holder assembly where the device further includes a security device to resist removal of the device from the first side rail The PED holder assembly where at least one of the first surface of the second surface includes a curved surface. The PED holder assembly where the curved surface includes a concave surface. The PED holder assembly where the curved surface includes a convex surface. The PED holder assembly where the first surface and the second surface are positionable with a separation of up to three inches, along the movement axis. The PED holder assembly where the first surface and second, when in the closed position, include a geometry capable of securely clamping without rotation, against the first side rail.

One general aspect includes a device for connecting to a rail of health care facility equipment, the device including a body and a first surface for positioning against a first side of the rail of the health care facility equipment. The device also includes a second surface for positioning against a second side of the rail, opposite the first side, when the device is installed on the side rail, the first surface or second surface positionable in (1) an open position where the first surface and the second surface are released to permit installation of the device on the rail and a (2) closed position where the first surface and second surface are positioned against the first side and the second side of the rail. The device also includes a positionable arm coupled to both the body and to an electronic device holder to enable positioning of the electronic device holder.

Implementations may include one or more of the following features. The device where the first surface is a planar surface opposite the second surface. The device where the second surface and the first surface each include a compressible layer that deforms when the second surface and the first surface are positioned with a force against the first side and the second side of the rail. The device where the compressible layer includes a rubber having a hardness in a range of twenty shore a to sixty shore a durometer. The device where the second surface includes a concave portion opposite the concave portion of the first surface. The device where the body includes one or more interfaces adapted for connection to at least one of a power or a data cable of a health care facility, the one or more interfaces communicatively coupleable to the electronic device or the electronic device holder. The device where the electronic device holder includes power and data connections for coupling the power and data cable of the health care facility with the electronic device. The device where the body includes a power converter configured to receive power input from a power cable of a health care facility and output a power output at a different voltage from a voltage of the power input. The device where the second surface is positionable in the open position and the closed position by actuating an actuation mechanism. The device where the actuation mechanism includes a threaded connection, a cam lever, or ratchet device.

For a fuller understanding of the nature and advantages of the present invention, reference should be made to the ensuing detailed description and accompanying drawings.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
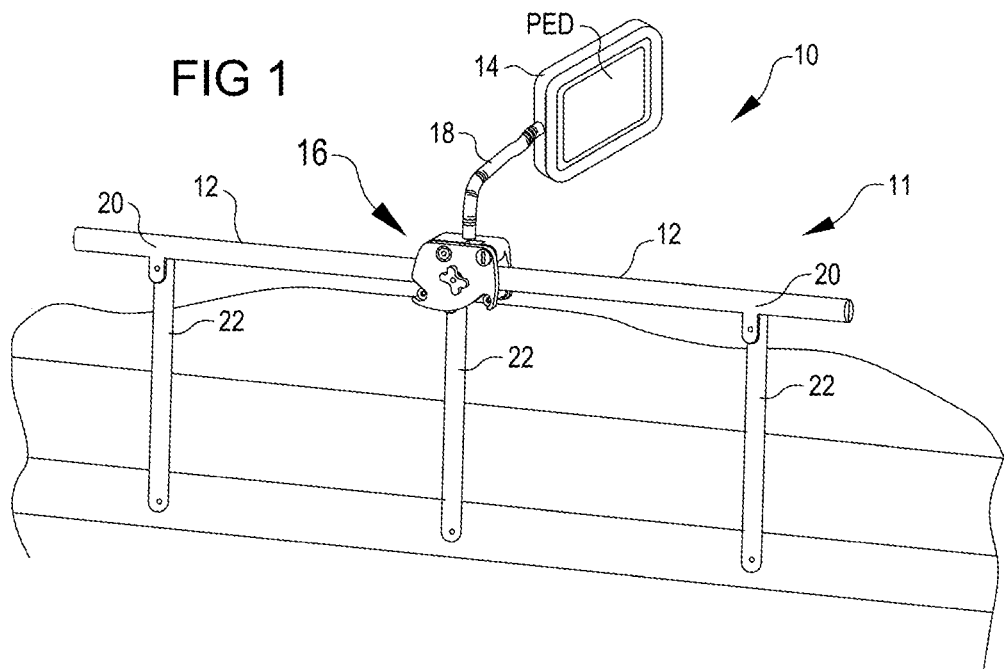
FIG. 1 shows a portable electronic device (PED) holder assembly that includes a bed connector that attaches to a side rail of the patient bed, in accordance with embodiments.

In the following description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

As is known, a hospital bed or hospital stretcher is a patient holder assembly specially designed for hospitalized patients or others in need of some form of health care. As used herein throughout this disclosure, a "bed" refers to any patient holder assembly. Hospital beds have special features both for the comfort and well-being of the patient and for the convenience of health care workers. Common features include adjustable height for the entire bed, the head, and the feet, adjustable side rails, and electronic buttons to operate both the bed and other nearby electronic devices. Hospital beds and other similar types of beds are used not only in hospitals, but in other health care facilities and settings, such as nursing homes, assisted living facilities, outpatient clinics, and in home health care.

Many hospital beds have side rails that can be raised or lowered. These rails serve as protection for the patient and sometimes can make the patient feel more secure. There are a variety of different types of side rails designed to prevent falls, provide security for the patient, and/or provide assistance for the patient getting in and out of the bed. The side rails may or may not move with a head portion of the bed that moves upward to allow reclining by a patient.

Some embodiments herein are directed to a portable electronic device (PED) holder assembly that includes a bed connector releasably attaching the PED holder assembly to a bed side rail, for example for a hospital bed. In many embodiments, the bed connector is configured to releasably and securely mount to the side rail. In many embodiments, the PED holder assembly includes a support arm that is attached to the bed connector and to a PED holder to which a PED is attached. The support arm is, in embodiments, articulating, flexible, rotatable, and/or otherwise configurable to allow positioning of the PED holder in a desired position relative to the patient on the bed and/or hospital staff adjacent to the bed. The PED holder can be any structure that can support a PED. The PED can be any suitable portable electronic device, for example, a mobile phone, a smart phone, a personal digital assistant (PDA), a laptop computer, a desktop computer, a thin-client device, a tablet PC, an electronic book (e-book) reader, or other computing devices or electronic devices.

In some embodiments, the bed connector is designed to fit securely onto a side rail of a hospital bed so that the bed connector does not rotate relative to the side rail. In one such an embodiment, the bed connector can fit over the side rail and a bar that extends at an angle to the side rail, with the bed connector engaging both sides of the bar so that limited rotational movement of the bed connector is permitted after installation.

Turning now to the drawing figures in which the same or similar reference identifiers refer to the same or similar components throughout all of the drawing figures, FIG. 1 shows a PED holder assembly 10 for attaching a PED to hospital bed side rail 11. The PED holder assembly 10 includes a PED holder 14 to which the PED is attachable, a bed connector 16 for attaching to the bed side rail 11, and a support arm 18 extending between the bed connector 16 and the PED holder 14. In FIG. 1, the bed connector 16 is shown attached to a junction 20 at the top edge of a top rail 12 of the side rail 11 for a hospital bed. The junction 20 is the junction of the top rail 12 and a bar 22 that extends downward from the top rail 12. While suitable embodiments of the PED holder assembly 10 are described herein, U.S. patent application Ser. No. 15/705,105, entitled "Electronic Device Mount for Releasably Attaching to Equipment in a Hospital Room," which is hereby incorporated herein by reference in its entirety, provides description of a device 10 that is applicable to some embodiments of the PED holder assembly 10.

The PED holder 14 can be any suitable structure that can support a PED. For example, the PED holder 14 can include a device clamp that holds two or more sides of a PED, a stand that permits a PED to sit on top, a mount for supporting or holding a PED, one or more magnets for magnetically connecting to a PED, a tether, or any other structure that can clamp, friction fit, balance, suspend, or otherwise connect to or support a PED. The PED holder 14 can be designed to hold several different sized or shaped PEDs, and could be as simple as a flat surface. In many embodiments described herein, a PED holder assembly includes at least one assistance request button that can be pressed to communicate a request for assistance to an attendant station (e.g., a nurse station).

Figure 2:
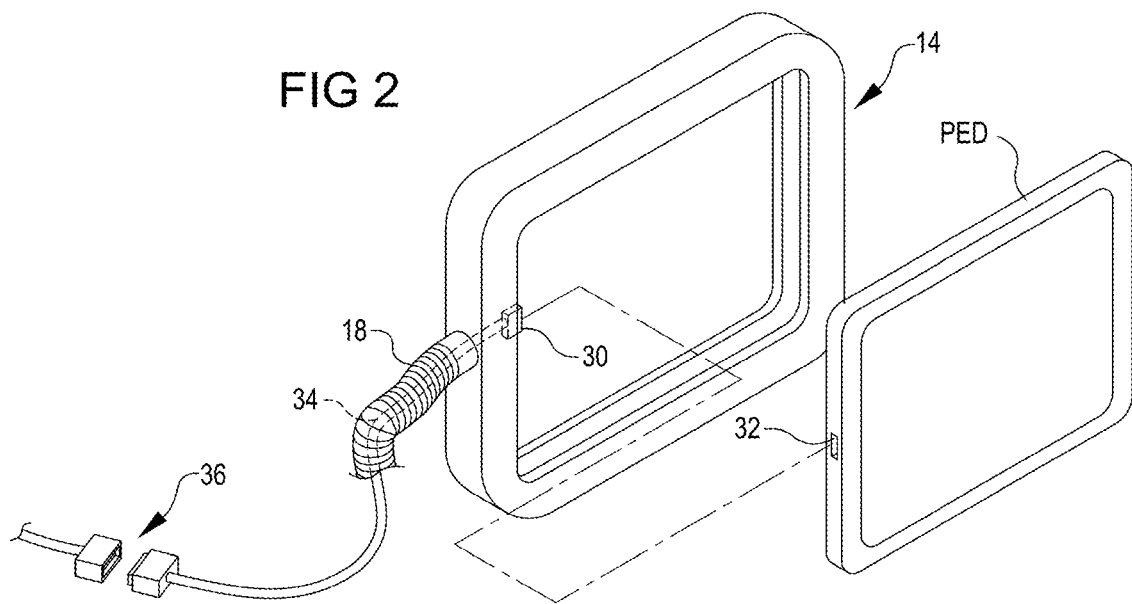
FIG. 2 shows some components of the PED holder assembly of FIG. 1.

In some embodiments, the PED holder assembly 10 include an electrical connector for providing power and/or data to the PED. In embodiments, such electrical connector includes a charging feature for fitting into a charging port or otherwise connecting to the PED to provide power and/or data to the PED. For example, as shown by FIG. 2, the PED holder 14 can include a power and/or data output connector 30 for fitting into an input port 32 of the PED. The input port 32 of the PED can have any suitable configuration and be used to supply power to the PED and/or communicate data to and/or from the PED. For example, the power and/or data output connector 30 and the input port 32 can have any suitable Universal Serial Bus (USB) configuration. In some embodiments, the PED holder assembly 10 includes a battery, such as a rechargeable battery, for charging and/or powering the PED.

Power and/or data (e.g., data for communication) can be provided to the PED through the input port 32 via the power and/or data output connector 30. In such embodiments, a wire or set of wires can extend through the support arm 18, can be wrapped around the support arm 18, or can extend from the PED holder 14 free of the support arm 18. For example, as shown in FIG. 2, a cable 34 having one or more wires extends through the support arm 18. In embodiments, the PED holder assembly 10 includes a releasable connector 36, such as a magnetic connector disclosed in U.S. Pat. No. 9,147,965 (which is hereby incorporated herein in its entirety by reference), that can be disconnected so as to permit free movement of the portion of the PED holder assembly 10 connected to the hospital bed during movement of the hospital bed or when the PED holder assembly 10 is disconnected from the hospital bed. As an alternative to a wired connection, the PED can receive communications wirelessly, and the PED can be removed for charging or replacement of batteries. In addition, cable-less charging of the PED can be provided at the PED holder 14.

The support arm 18 is, in embodiments, articulating, flexible, rotatable, and/or otherwise configurable to allow positioning of the PED holder 14 in a desired position and orientation relative to the patient. In embodiments in which the support arm 18 is movable while the bed connector 16 remains anchored to the side rail 11, the support arm 18 and the PED holder 14 can be moved to a position out of the way in an emergency, but yet the PED holder 14 is still supported by the bed connector 16 via the side rail 11. In embodiments, the support arm 18 is not only reconfigurable to vary the position and/or orientation of the PED holder 14, but also retains the PED holder 14 in a selected position and orientation, such as over a patient or out to the side of a hospital bed for access by a caregiver. To this end, the support arm 18 can include sliding, locking pieces that accommodate repositioning and reorientation of the PED holder 14 and retain a selected position and orientation of the PED holder 14, or can have a flexible nature that resists, but allows, bending along its length. For example, the support arm 18 can include flexible adjustable shafts, such as those found in gooseneck lamps. As another example, the support arm 18 can include a coiled metal tube that is reconfigurable via selective bending along the length of the coiled metal tube.

Figure 3:
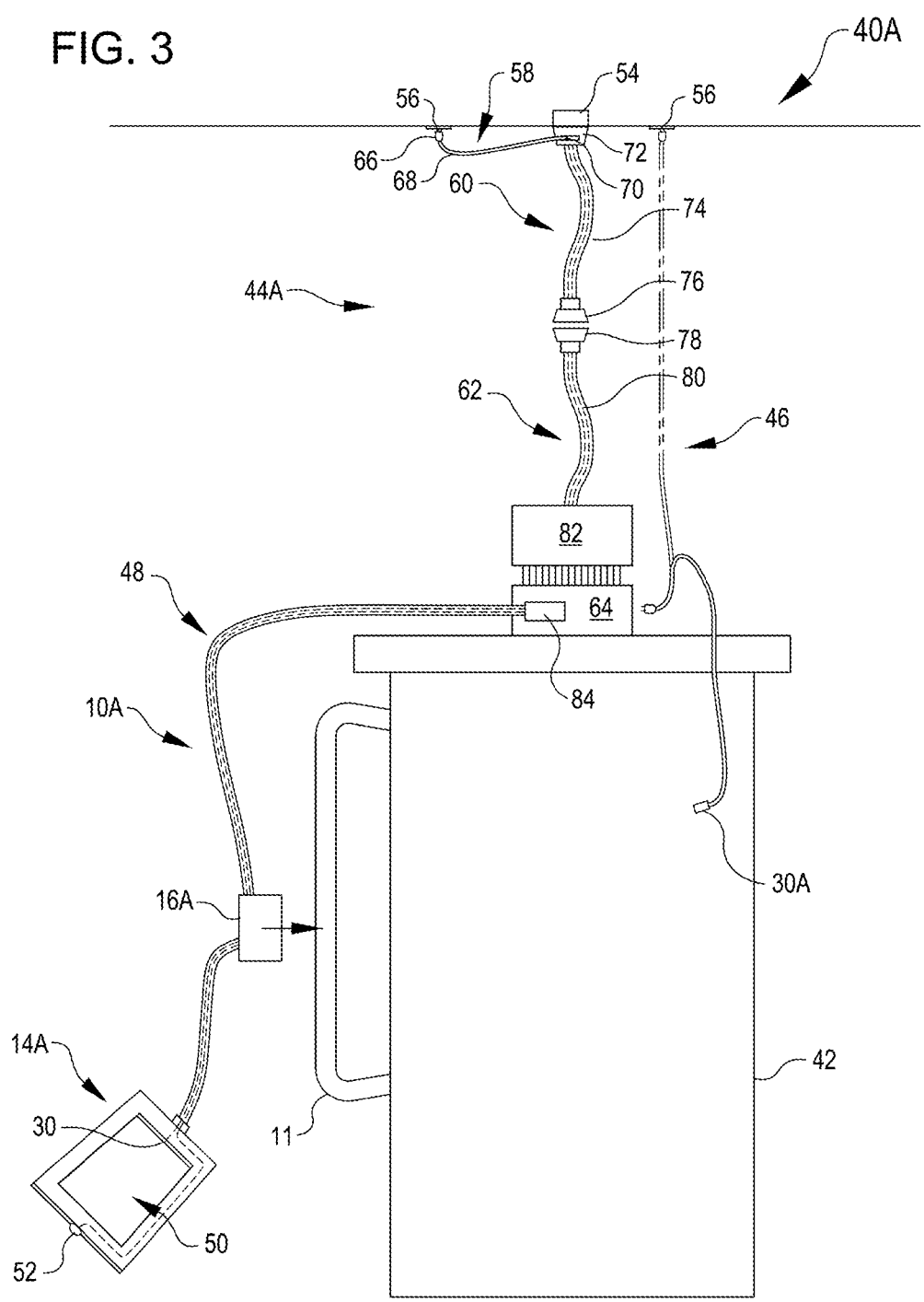
FIG. 3 shows a hospital room configuration in which a PED holder assembly is connected to a communication and power assembly for a patient bed, in accordance with embodiments.

FIG. 3 shows a hospital room configuration 40A that includes a hospital bed 42 having a side rail 11, a communication and power assembly 44A for the hospital bed 42, a PED holder assembly 10A, and, in some embodiments, a PED power and/or data cable assembly 46. The PED holder assembly 10A is configured similar to the PED holder assembly 10. For example, reference identifiers associated with components of PED holder assembly 10A that are the same or similar to components of the PED holder assembly 10 are the same or similar to reference identifiers associated with the components of the PED holder assembly 10. The PED holder assembly 10A includes a PED holder 14A, a bed connector 16A, and a power and/or data cable assembly 48. The PED holder 14A has a recess 50 shaped and sized to accommodate and hold a PED placed in the recess 50. In some embodiments, the PED holder 14A includes suitable retention features that retain the PED in the recess 50 to prevent inadvertent detachment of the PED from the PED holder 14A and accommodate intentional removal of the PED from the PED holder 14A. The PED holder 14A includes a power and/or data output connector 30 for fitting into an input port 32 of a PED held by the PED holder 14A. The PED holder 14A further includes a assistance request button 52 that can be pressed to communicate a request for assistance to an attendant station. The power and/or data cable assembly 48 operatively connects the power and/or data output connector 30 to the communication and power assembly 44A. The bed connector 16A is attachable to the side rail 11. The bed connector 16A is attached to, or attachable to, the power and/or data cable assembly 48 to retain the power and/or data cable assembly 48 within reach of a patient in the bed 42. In some embodiments, the distal end of the cable assembly 48 is securely attached to the PED holder 14A so that the patient can grab and pull on the cable assembly 48 to bring the PED holder 14A within reach of the patient when the patient wants to use the PED and/or press the assistance request button 52 to request assistance. In some embodiments, the PED holder assembly 10A includes a support arm the same as, or similar to, the support arm 18 of the PED holder assembly 10 to support the PED holder 14A in a selected position and orientation relative to the bed connector 16A.

In some embodiments, the communication and power assembly 44A operatively connects the bed 42 to a assistance request communication system hub 54 and connects the PED holder assembly 10A to a power and/or data outlet 56. The assistance request communication system hub 54 is operatively connected to a assistance request communication system that is operable to transmit a assistance request signal generated via operation of the assistance request button 52 to an attendant station. The power and/or data outlet 56 supplies power and/or data to a PED held by the PED holder assembly 10A through the communication and power assembly 44A and the cable assembly 48. The communication and power assembly 44A includes a PED power and/or data cable assembly 58, a proximal cable assembly 60, a distal cable assembly 62, and an intermediate connector 64 mounted to the bed 42. The PED power and/or data cable assembly 58 includes a proximal connector 66, a power and/or data cable 68, and a distal connector 70. The proximal cable assembly 60 includes a proximal connector 72, a power/communication cable 74, and a distal connector 76. The distal cable assembly 62 includes a proximal connector 78, a power/communication cable 80, and a distal connector 82. The proximal connector 66 of the cable assembly 58 is connectable to the power and/or data outlet 56 and the distal connector 70 of the cable assembly 58 is connectable to the proximal connector 72 of the cable assembly 60 to operatively connect the communication and power assembly 44A to the power and/or data outlet 56. The proximal connector 72 of the cable assembly 60 is connectable to the hub 54 to operatively connect the communication and power assembly 44A to the assistance request communication system. The proximal connector 78 of the cable assembly 62 is connectable to the distal connector 76 of the cable assembly 60 to operatively connect the cable assembly 62 to the assistance request communication system and the outlet 56. The distal connector 82 of the cable assembly 62 is connectable to the intermediate connector 64 to operatively connect the intermediate connector 64 to the assistance request communication system and the power and/or data outlet 56. The power and/or data cable assembly 48 includes a proximal connector 84 that is connectable to the intermediate connector 64 to operatively connect the power and/or data cable assembly 48 to the assistance request communication system and the outlet 56.

In some embodiments, the communication and power assembly 44A operatively connects the intermediate connector 64 to the assistance request communication system hub 54 and the intermediate connector 64 is operatively connected to a power and/or data outlet 56 via the PED power and/or data cable assembly 46. In the illustrated embodiment, the PED power and/or data cable assembly 46 includes a distal power and/or data output connector 30A, which can be connected to an input port 32 of a PED to operatively connect the PED to the power and/or data outlet 56.

In some embodiments, the communication and power assembly 44A is configured to enable quick disconnection of the bed 42 from the assistance request communication system hub 54 and the power and/or data outlet 56 when the bed 42 needs to be moved. For example, the distal connector 76 and the proximal connector 78 can form a releasable magnetic connection, such as the magnetic connector disclosed in U.S. Pat. No. 9,147,965. As another example, the distal connector 82 and the intermediate connector 64 can form a releasable magnetic connection, such as the magnetic connector disclosed in U.S. Pat. No. 9,147,965.

Figure 4:
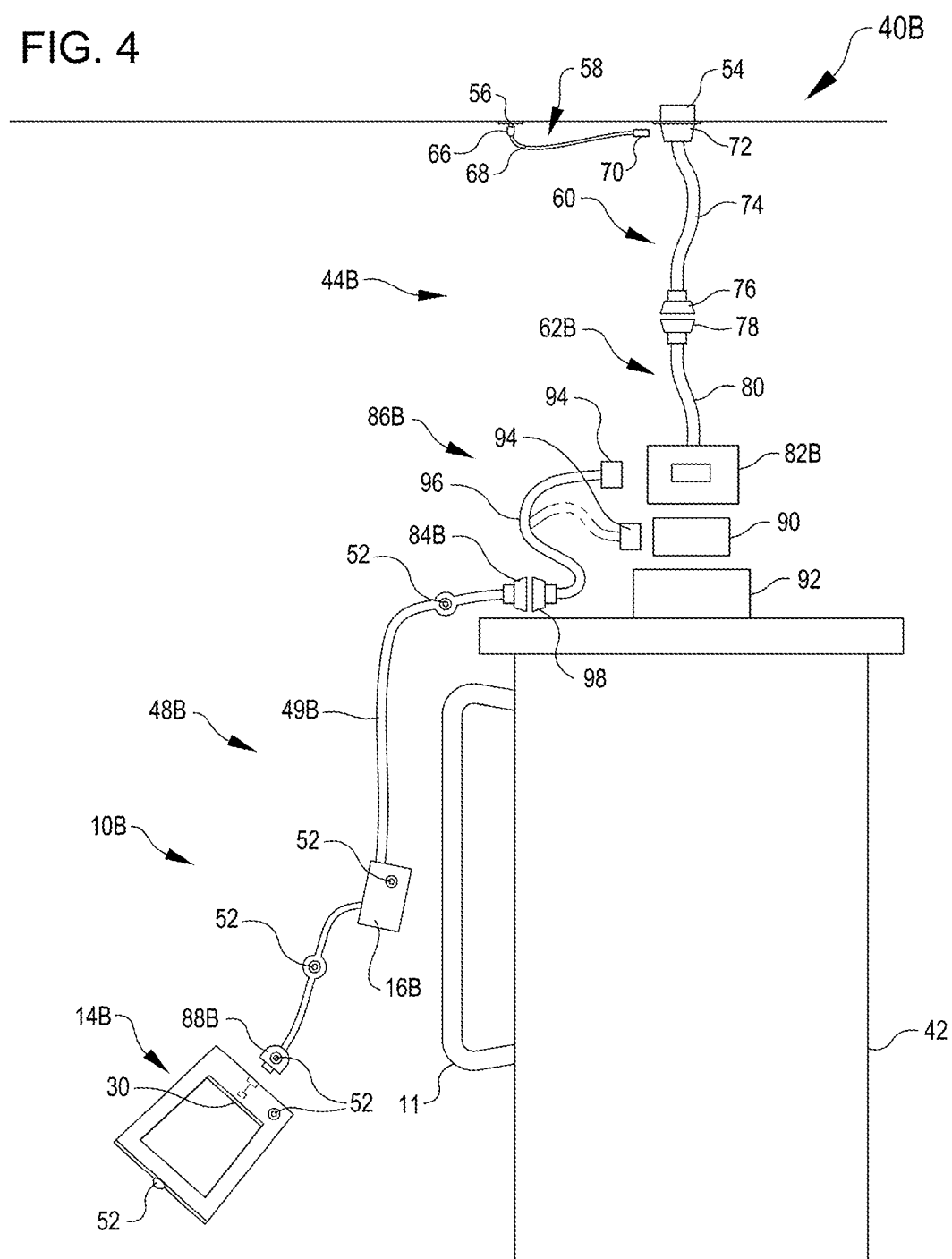
FIG. 4 shows a hospital room configuration in which a PED holder assembly is connected to a communication and power assembly for a patient bed, in accordance with embodiments, the PED holder assembly including one or more assistance request buttons.

FIG. 4 shows a hospital room configuration 40B that includes a hospital bed 42 having a side rail 11, a communication and power assembly 44B for the hospital bed 42, an intermediate connector assembly 86B, and a PED holder assembly 10B. The PED holder assembly 10B is configured similar to the PED holder assembly 10. For example, reference identifiers associated with components of PED holder assembly 10B that are the same or similar to components of the PED holder assembly 10 are the same or similar to reference identifiers associated with the components of the PED holder assembly 10. The PED holder assembly 10B includes a PED holder 14B, a bed connector 16B, and a power and/or data cable assembly 48B. The PED holder 14B has a recess 50 shaped and sized to accommodate and hold a PED placed in the recess 50. In some embodiments, the PED holder 14B includes suitable retention features that retain the PED in the recess 50 to prevent inadvertent detachment of the PED from the PED holder 14B and accommodate intentional removal of the PED from the PED holder 14B. The PED holder 14B includes a power and/or data output connector 30 for fitting into an input port 32 of a PED held by the PED holder 14B. The PED holder 14B can include any suitable number of assistance request buttons 52 that can be pressed to communicate a request for assistance to an attendant station. For example, in the illustrated embodiment, the PED holder 14B includes two assistance request buttons 52. The power and/or data cable assembly 48B operatively connects the power and/or data output connector 30 and the assistance request buttons 52 to the intermediate cable assembly 86B. The power and/or data cable assembly 48B can include any suitable number of assistance request buttons 52 that can be pressed to communicate a request for assistance to an attendant station. For example, in the illustrated embodiment, the power and/or data cable assembly 48B includes three assistance request buttons 52 distributed along the length of the power and/or data cable assembly 48B. The power and/or data cable assembly 48B includes a distal connector 88B that is connectable to the PED holder 14B to operatively couple the PED holder 14B to the power and/or data cable assembly 48B. In the illustrated embodiment, the distal connector 88B includes a assistance request buttons 52 that can be pressed to communicate a request for assistance to an attendant station. The bed connector 16B is attachable to the side rail 11. The bed connector 16B is attached to, or attachable to, the power and/or data cable assembly 48B to retain the power and/or data cable assembly 48B within reach of a patient in the bed 42 so that the patient can grab and pull on the cable assembly 48 to bring the PED holder 14B within reach of the patient when the patient wants to use the PED and/or press the assistance request button 52 to request assistance. In some embodiments, the PED holder assembly 10B includes a support arm the same as, or similar to, the support arm 18 of the PED holder assembly 10 to support the PED holder 14B in a selected position and orientation relative to the bed connector 16B.

The communication and power assembly 44B operatively connects the intermediate cable assembly 86B to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder assembly 10B through the communication and power assembly 44B, the intermediate cable assembly 86B, and the cable assembly 48B. The communication and power assembly 44B includes the PED power and/or data cable assembly 58, the proximal cable assembly 60, a distal cable assembly 62B, and a coupler 90. The distal cable assembly 62B includes the proximal connector 78, the power/communication cable 80, and a distal connector 82B. The proximal connector 66 of the cable assembly 58 is connectable to the outlet 56 and the distal connector 70 of the cable assembly 58 is connectable to the proximal connector 72 of the cable assembly 60 to operatively connect the communication and power assembly 44B to the power and/or data outlet 56. The proximal connector 72 of the cable assembly 60 is connectable to the assistance request hub 54 to operatively connect the communication and power assembly 44B to the assistance request communication system. The proximal connector 78 of the cable assembly 62B is connectable to the distal connector 76 of the cable assembly 60 to operatively connect the cable assembly 62B to the assistance request communication system and the outlet 56. The distal connector 82B of the cable assembly 62 is connectable to the coupler 90 to operatively connect the coupler 90 to the assistance request communication system and the outlet 56. The bed 42 includes a bed hub 92 to which the coupler 90 is connectable to operatively connect the bed hub 92 to the assistance request communication system and/or the outlet 56. In some embodiments, the bed 42 includes any suitable number of assistance request buttons 52 that are operatively coupled with the assistance request communication system via the bed hub 92.

The intermediate cable assembly 86B operatively connects the PED holder assembly 10B to the assistance request communication system hub 54 and the outlet 56. The intermediate cable assembly 86B includes a proximal connector 94, a cable 96 operatively connected to the proximal connector 94, and a distal connector 98 operatively connected to the cable 96. In some embodiments, the proximal connector 94 is connectable to the distal connector 82B to operatively connect the intermediate cable assembly 86 to the assistance request communication system and the outlet 56 via the communication and power assembly 44B. In some embodiments, the proximal connector 94 is connectable to the coupler 90 to operatively connect the intermediate cable assembly 86 to the assistance request communication system and the outlet 56 via the communication and power assembly 44B.

The cable assembly 48B operatively connects the PED holder 14B to the assistance request communication system hub 54 and the outlet 56. The cable assembly 48B includes a proximal connector 84B, a cable 49B operatively connected to the proximal connector 84B, and the distal connector 88B operatively connected to the cable 49B. The proximal connector 84B is connectable to the distal connector 98 to operatively connect the cable assembly 48B to the assistance request communication system and the outlet 56 via the intermediate cable assembly 86B and the communication and power assembly 44B.

The hospital room configuration 40B can include any suitable number of quick disconnection features that enhance the ability to move the bed 42 and/or the PED holder assembly 10B. For example, in some embodiments, the distal connector 76 and the proximal connector 78 form a quick release connection, such as the magnetic connector disclosed in U.S. Pat. No. 9,147,965. In some embodiments, the distal connector 98 and the proximal connector 84B form a quick release connection, such as the magnetic connector disclosed in U.S. Pat. No. 9,147,965.

Figure 5:
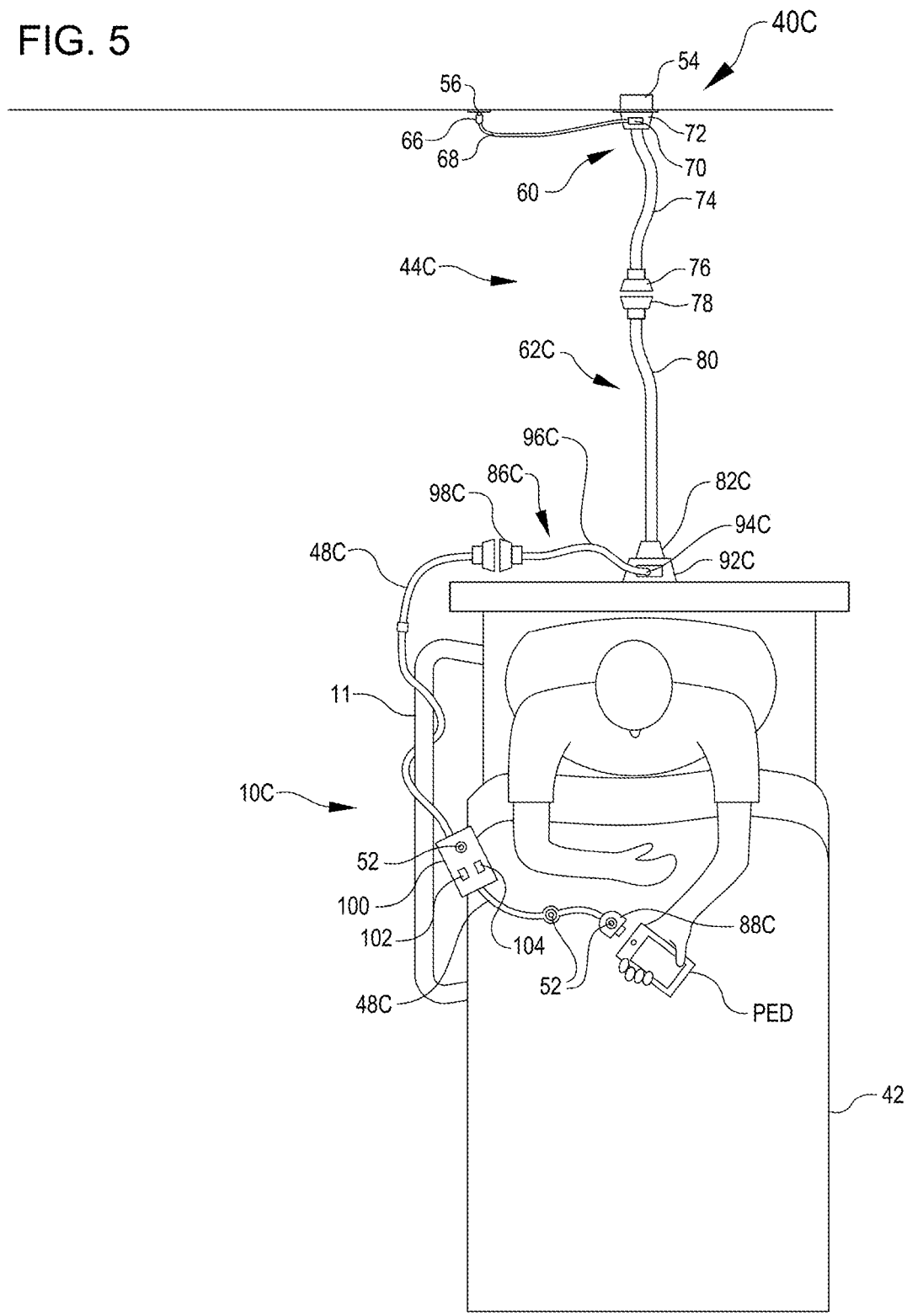
FIG. 5 shows a hospital room configuration in which a communication and power assembly for use by a patient is connected to a communication and power assembly for a patient bed, in accordance with embodiments.

FIG. 5 shows a hospital room configuration 40C that includes a hospital bed 42 having a side rail 11, a communication and power assembly 44C for the hospital bed 42, an intermediate connector assembly 86C, and a assistance request/PED cable assembly 10C. The assistance request/PED cable assembly 10C is configured similar to the PED holder assembly 10B, but without the PED holder 14B. For example, reference identifiers associated with components of assistance request/PED cable assembly 10C that are the same or similar to components of the PED holder assembly 10B are the same or similar to reference identifiers associated with the components of the PED holder assembly 10B. The assistance request/PED cable assembly 10C includes a proximal connector 84C, a cable assembly 48C, a patient interface unit 100, and a distal connector 88C. The distal connector 88C is a power and/or data output connector for fitting into an input port 32 of a PED. The distal connector 88C operatively connects the PED to the assistance request/PED cable assembly 10C. The cable assembly 48C can include any suitable number of assistance request buttons 52 that can be pressed to communicate a request for assistance to an attendant station. For example, in the illustrated embodiment, the cable assembly 48C includes one assistance request button located between the patient interface unit 100 and the distal connector 88C. The distal connector 88C also includes a assistance request buttons 52 that can be pressed to communicate a request for assistance to an attendant station. The patient interface unit 100 includes a assistance request button 52 and can include any suitable patient input devices, such as a remote control input devices for a television. In some embodiments, the cable assembly 48C can be wrapped around the side rail 11 to retain the cable assembly 48C within reach of a patient in the bed 42 when the patient wants to use the PED and/or press the assistance request button 52 to request assistance.

The communication and power assembly 44C operatively connects the intermediate cable assembly 86C to the assistance request communication system hub 54 and the outlet 56 and connects the bed 42 to the assistance request communication system hub 54 and, in some embodiments, the outlet 56. The power and/or data outlet 56 supplies power and/or data to a PED connected to the assistance request/PED cable assembly 10C through the communication and power assembly 44C, the intermediate cable assembly 86C, and the cable assembly 48C. The communication and power assembly 44C includes the PED power and/or data cable assembly 58, the proximal cable assembly 60, and a distal cable assembly 62C. The distal cable assembly 62C includes the proximal connector 78, the power/communication cable 80, and a distal connector 82C. The proximal connector 66 of the cable assembly 58 is connectable to the outlet 56 and the distal connector 70 of the cable assembly 58 is connectable to the proximal connector 72 of the cable assembly 60 to operatively connect the communication and power assembly 44C to the power and/or data outlet 56. The proximal connector 72 of the cable assembly 60 is connectable to the hub 54 to operatively connect the communication and power assembly 44C to the assistance request communication system. The proximal connector 78 of the cable assembly 62C is connectable to the distal connector 76 of the cable assembly 60 to operatively connect the cable assembly 62C to the assistance request communication system and the outlet 56. The bed 42 includes a bed hub 92C to which the distal connector 82C is connectable to operatively connect the bed hub 92C to the assistance request communication system and/or the outlet 56. In some embodiments, the bed 42 includes any suitable number of assistance request buttons 52 that are operatively coupled with the assistance request communication system via the bed hub 92C.

The intermediate cable assembly 86C operatively connects the assistance request/PED cable assembly 10C to the assistance request communication system hub 54 and the outlet 56 via the communication and power assembly 44C. The intermediate cable assembly 86C includes a proximal connector 94C, a cable 96C operatively connected to the proximal connector 94C, and a distal connector 98C operatively connected to the cable 96C. The proximal connector 94C is connectable to the bed hub 92C to operatively connect the intermediate cable assembly 86C to the assistance request communication system and the outlet 56 via the communication and power assembly 44C.

The hospital room configuration 40C can include any suitable number of quick disconnection features that enhance the ability to move the bed 42 and/or the assistance request/PED cable assembly 10C. For example, in some embodiments, the distal connector 76 and the proximal connector 78 form a quick release connection, such as the magnetic connector disclosed in U.S. Pat. No. 9,147,965. In some embodiments, the distal connector 98C and the proximal connector 84C form a quick release connection, such as the magnetic connector disclosed in U.S. Pat. No. 9,147,965.

Figure 6:
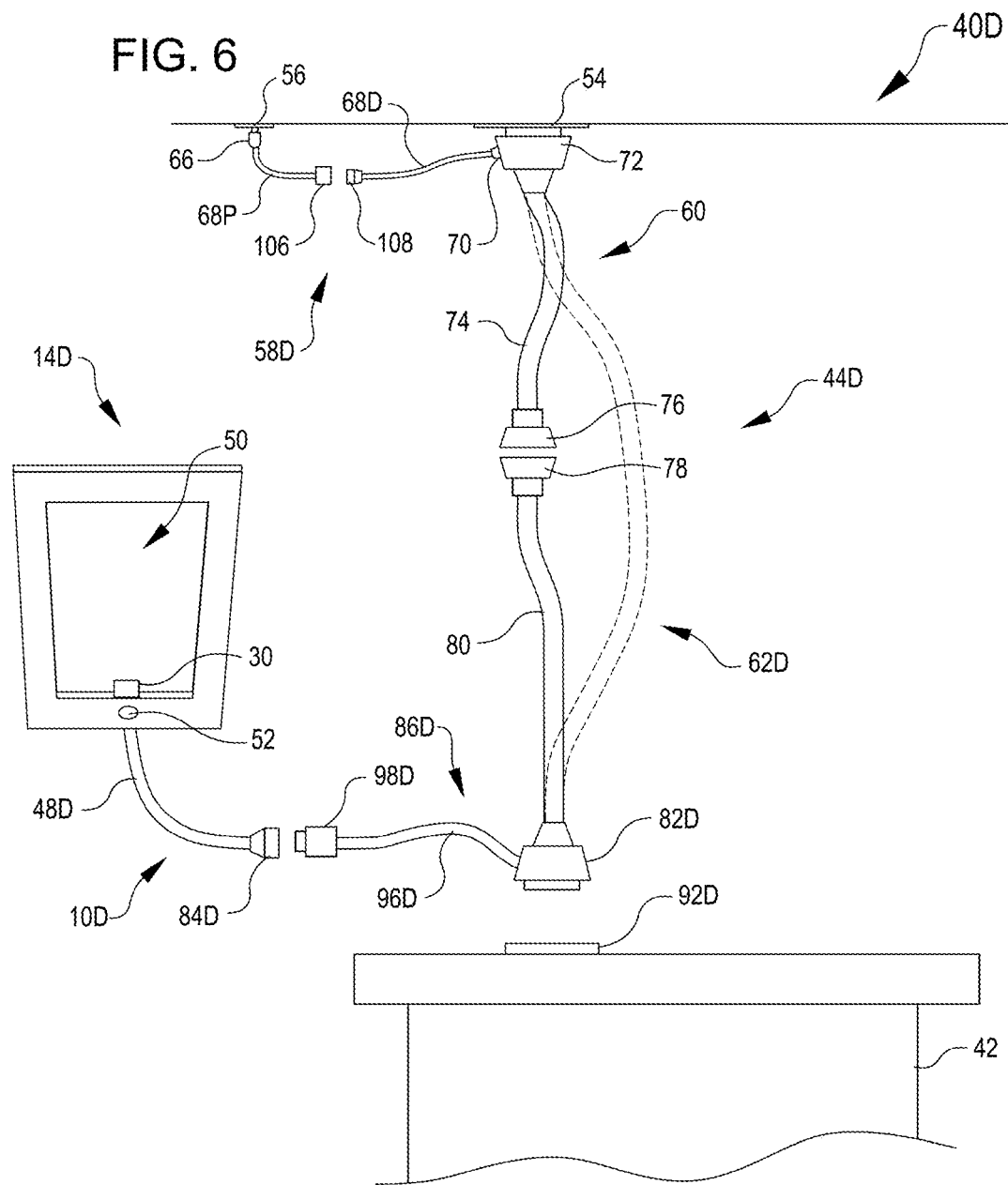
FIG. 6 shows a hospital room configuration in which a PED holder assembly is connected to a communication and power assembly for a patient bed, in accordance with embodiments, the PED holder assembly including a assistance request button.

FIG. 6 shows a hospital room configuration 40D that includes a hospital bed 42, a communication and power assembly 44D for the hospital bed 42, and a PED holder assembly 10D. The communication and power assembly 44D is configured similar to the communication and power assembly 44C, but including an intermediate connector assembly 86D that is integral to the distal cable assembly 62C. For example, reference identifiers associated with components of the communication and power assembly 44D that are the same or similar to components of the communication and power assembly 44C are the same or similar to reference identifiers associated with the components of the communication and power assembly 44C. The PED holder assembly 10D includes a proximal connector 84D, a cable assembly 48D, and a PED holder 14D. The PED holder assembly 10D is configured similar to the PED holder assembly 10. For example, reference identifiers associated with components of PED holder assembly 10D that are the same or similar to components of the PED holder assembly 10 are the same or similar to reference identifiers associated components of the PED holder assembly 10. The PED holder 14D can include any suitable number of assistance request buttons 52 that can be pressed to communicate a request for assistance to an attendant station. For example, in the illustrated embodiment, the PED holder 14D includes a single assistance request button 52.

The communication and power assembly 44D operatively connects the PED holder assembly 10D to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder 14D through the communication and power assembly 44D. The communication and power assembly 44D includes a PED power and/or data cable assembly 58D, the proximal cable assembly 60, and a distal cable assembly 62D. The distal cable assembly 62D includes the proximal connector 78, the power/communication cable 80, a distal connector 82D, and the intermediate connector assembly 86D. The PED power and/or data cable assembly 58D includes the proximal connector 66, a proximal cable 68P, a connector 106, a connector 108, a distal cable 68D, and the distal connector 70. The proximal connector 66 is connectable to the outlet 56, the connector 108 is connectable to the connector 106, and the distal connector 70 is connectable to the proximal connector 72 of the cable assembly 60 to operatively connect the communication and power assembly 44D to the power and/or data outlet 56. The proximal connector 72 of the cable assembly 60 is connectable to the assistance request hub 54 to operatively connect the communication and power assembly 44D to the assistance request communication system. The proximal connector 78 of the cable assembly 62D is connectable to the distal connector 76 of the cable assembly 60 to operatively connect the cable assembly 62D to the assistance request communication system and the outlet 56. The bed 42 includes a bed hub 92D to which the distal connector 82D is connectable to operatively connect the bed hub 92D to the assistance request communication system and/or the outlet 56. In some embodiments, the bed 42 includes any suitable number of assistance request buttons 52 that are operatively coupled with the assistance request communication system via the bed hub 92D. In some embodiments of the communication and power assembly 44D, the connectors 76, 78 are omitted and a single cable segment connects the connectors 72, 82D.

The intermediate cable assembly 86D operatively connects the PED holder assembly 10D to the assistance request communication system hub 54 and the outlet 56. The intermediate cable assembly 86C includes a cable 96D and a distal connector 98D operatively connected to the cable 96C. The cable 96D is operatively connected to the connector 82D and extends from the connector 82D.

The hospital room configuration 40D can include any suitable number of quick disconnection features that enhance the ability to move the bed 42 and/or the PED holder assembly 10D. For example, in some embodiments, the distal connector 76 and the proximal connector 78 form a quick release connection, such as the magnetic connector disclosed in U.S. Pat. No. 9,147,965. In some embodiments, the distal connector 98D and the proximal connector 84D form a quick release connection, such as the magnetic connector disclosed in U.S. Pat. No. 9,147,965.

Figure 7:
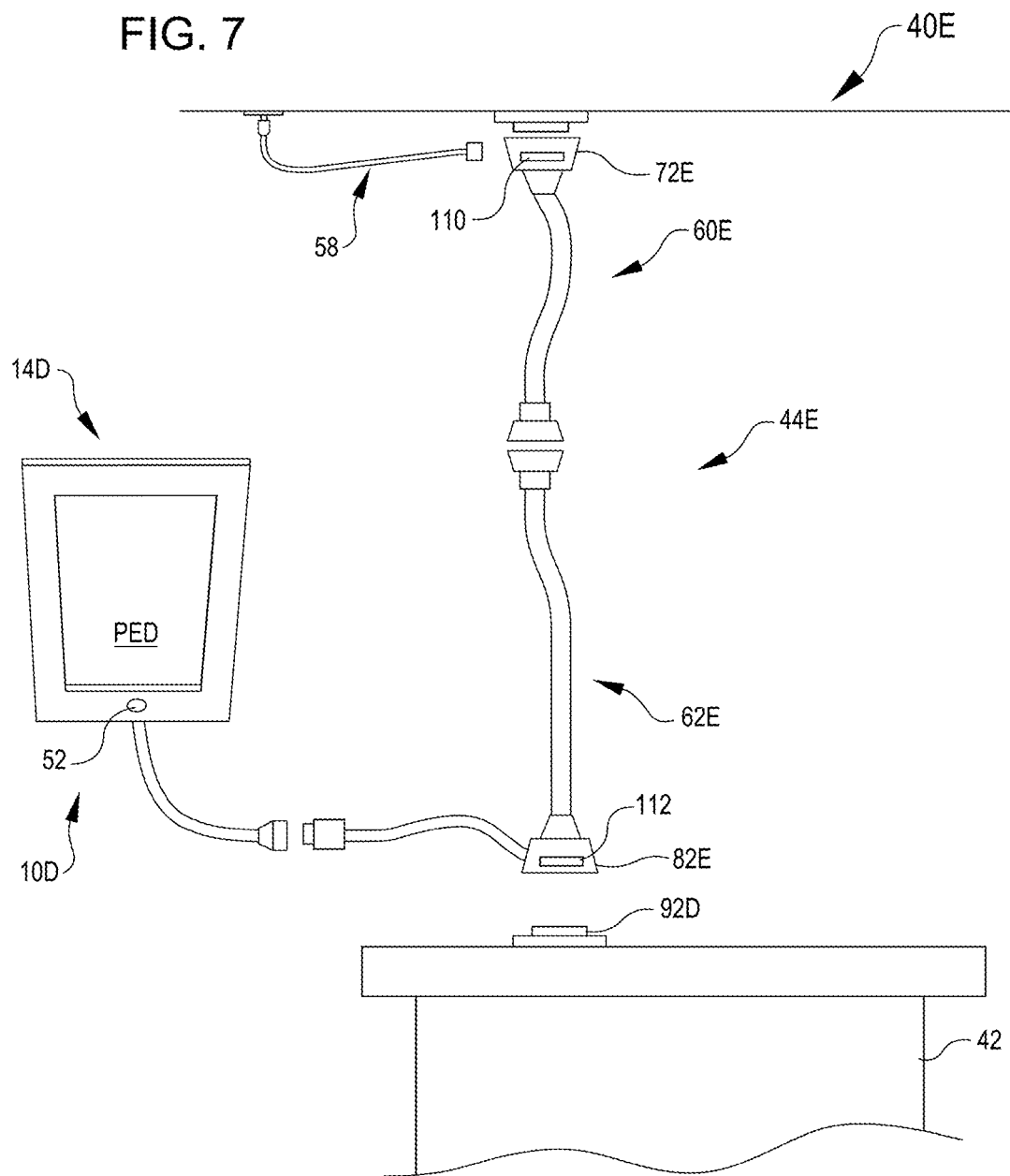
FIG. 7 shows a hospital room configuration in which a PED holder assembly is connected to a communication and power assembly for a patient bed, in accordance with embodiments, the PED holder assembly including a assistance request button.

FIG. 7 shows a hospital room configuration 40E that is similar to the hospital room configuration 40D except for differences described below. Reference identifiers associated with components of the hospital room configuration 40E that are the same or similar to components of the hospital room configuration 40D are the same or similar to reference identifiers associated with the components of the hospital room configuration 40D. The hospital room configuration 40E includes the one-piece PED power and/or data cable assembly 58 shown in FIG. 4 as opposed to the two-piece PED power and/or data cable assembly 58D shown in FIG. 6. The hospital room configuration 40E employs a communication and power assembly 44E as opposed to the communication and power assembly 44D shown in FIG. 6. The communication and power assembly 44E includes a proximal cable assembly 60E and a distal cable assembly 62E. The proximal cable assembly 60E is similar to the proximal cable assembly 60D, but has a proximal connector 72E that includes a power/data output port 110 to which a PED can be connected via a suitable connection cable. The distal cable assembly 62E is similar to the distal cable assembly 62E, but has a distal connector 82E that includes a power/data output port 112 to which a PED can be connected via a suitable connection cable.

Figure 8:
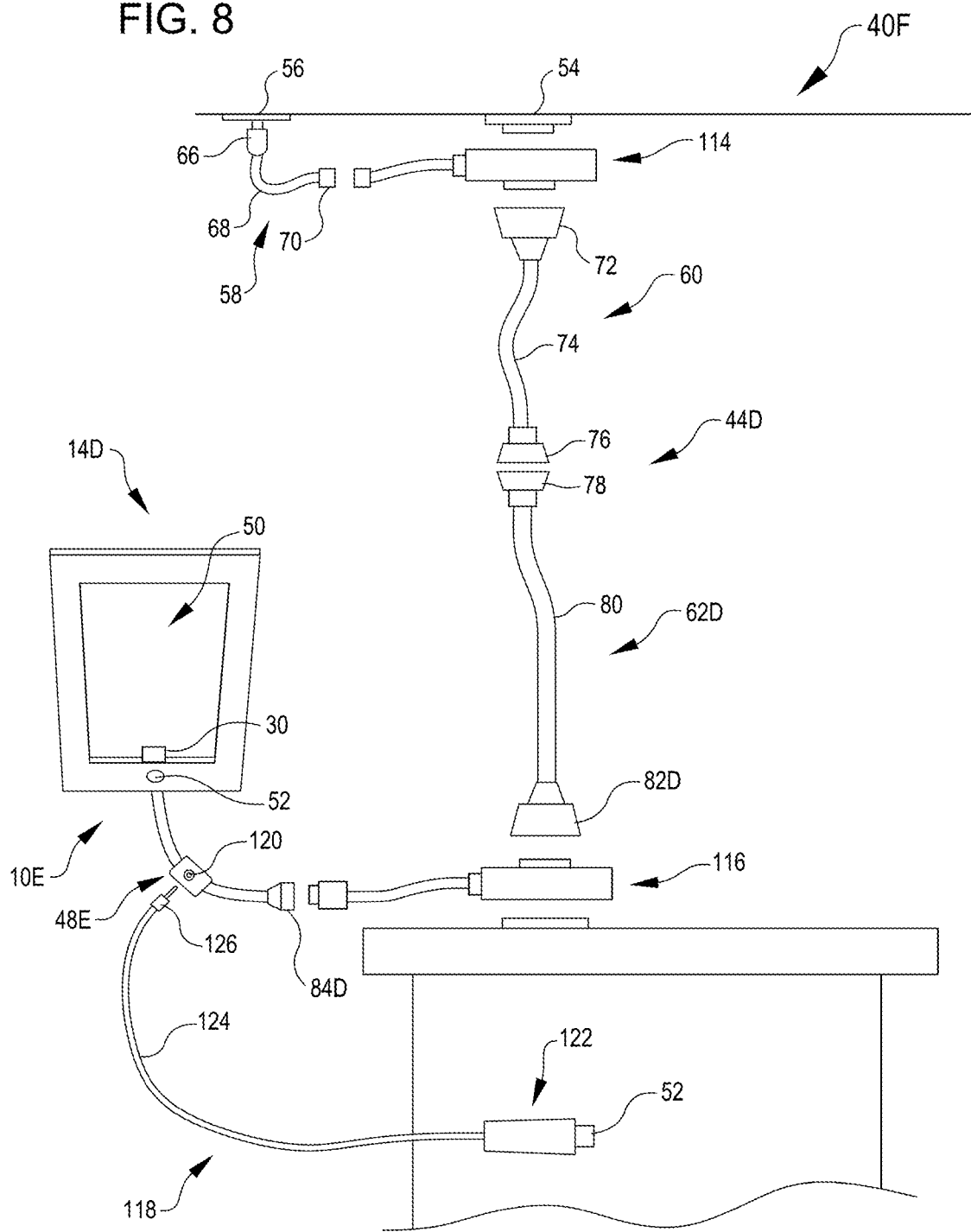
FIG. 8 shows a hospital room configuration in which a PED holder assembly is connected to a communication and power assembly for a patient bed, in accordance with embodiments, the PED holder assembly including a connection port for a assistance request button assembly.

FIG. 8 shows a hospital room configuration 40F that is similar to the hospital room configuration 40D except for differences described below. Reference identifiers associated with components of the hospital room configuration 40F that are the same or similar to components of the hospital room configuration 40D are the same or similar to reference identifiers associated with the components of the hospital room configuration 40D. The hospital room configuration 40F includes a proximal coupler 114 and a distal coupler 116. The proximal coupler 114 is connectable to and between the proximal connector 72 and the assistance request hub 54 to operatively couple the communication and power assembly 44D to the assistance request hub 54. Additionally, the proximal coupler 114 operatively couples the communication and power assembly 44D to the PED power and/or data cable assembly 58. The distal coupler 116 is connectable to and between the distal coupler 82D and the bed hub 92D to operatively coupled the bed 42 to the assistance request hub 54, and in some embodiments, to the power and/or data outlet 56. Additionally, the distal coupler 116 is connectable to and between the distal coupler 82D and the proximal connector 84D of the PED holder assembly 10E to operatively couple the PED holder assembly 10E to the assistance request hub 54 and the power and/or data outlet 56. The PED holder assembly 10E is configured similar to the PED holder assembly 10D shown in FIG. 6, but includes a assistance request cable assembly 118 and a connection port 120 to which the assistance request cable assembly 118 can be operatively connected to the assistance request hub 54. The assistance request cable assembly 118 includes a assistance request button assembly 122, a cable 124, and a proximal connector 126 connected to the assistance request button assembly 112 by the cable 124. The assistance request button assembly 122 includes a assistance request button 52 that can be pressed by a patient to communicate a request for assistance to an attendant station.

The hospital room configuration 40F can include any suitable number of quick disconnection features that enhance the ability to move the bed 42 and/or the PED holder assembly 10E. For example, in some embodiments, the distal connector 76 and the proximal connector 78 form a quick release connection, such as the magnetic connector disclosed in U.S. Pat. No. 9,147,965. In some embodiments, the proximal coupler 114 forms part of a quick release connection, such as the magnetic connector disclosed in U.S. Pat. No. 9,147,965. In some embodiments, the distal coupler 116 forms part of a quick release connection, such as the magnetic connector disclosed in U.S. Pat. No. 9,147,965.

Figure 9:
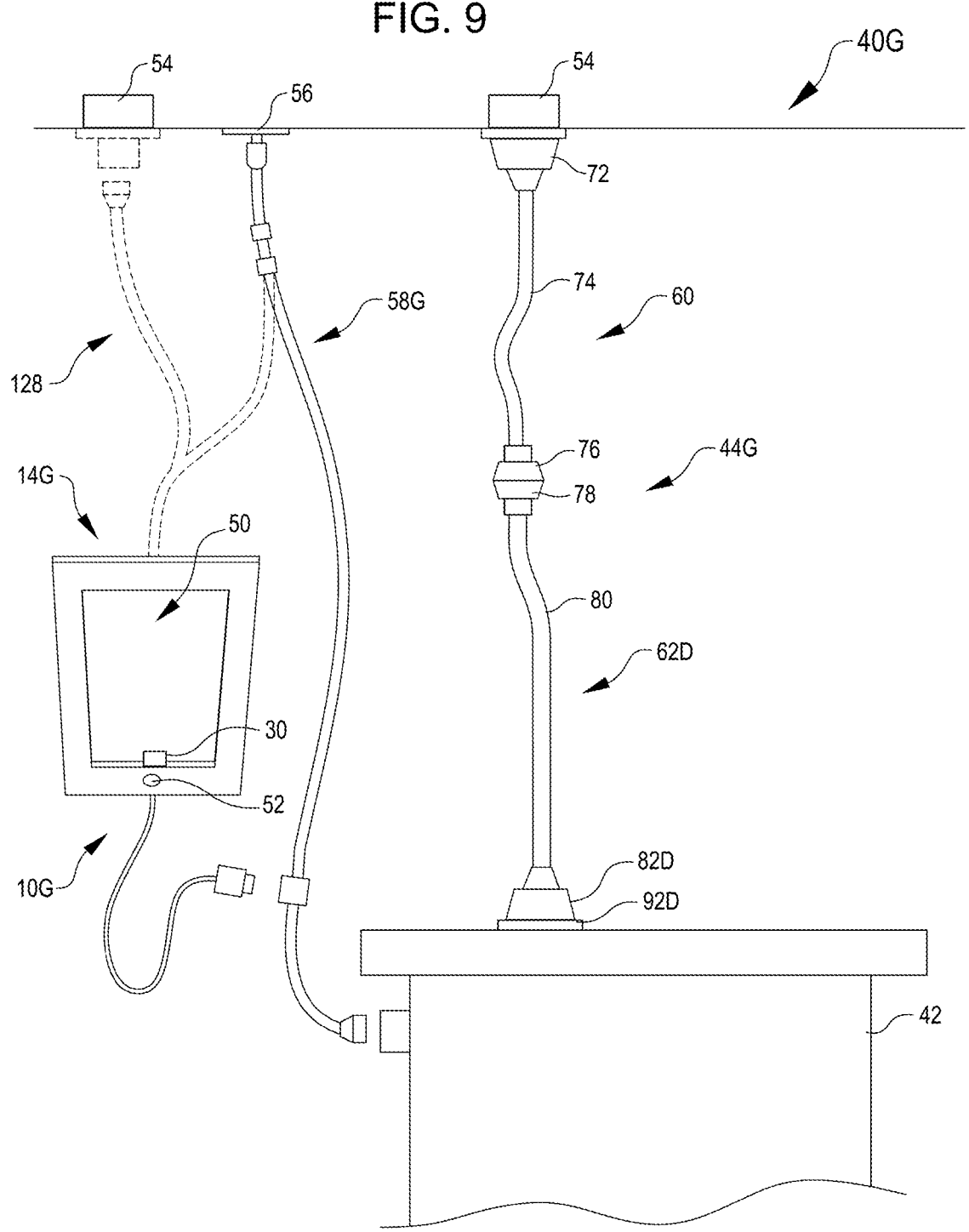
FIG. 9 shows a hospital room configuration that includes a PED holder assembly that can be connected to a communication and power assembly for a patient bed or connected directly to a power and/or data device that supplies power and/or data to a PED, in accordance with embodiments, the PED holder assembly including a assistance request button.

FIG. 9 shows a hospital room configuration 40G in which the bed 42 is coupled to the assistance request hub 54 via a assistance request communication cable assembly 44G. In some embodiments, the bed 42 is separately coupled to a power and/or data output 56 via a cable assembly 58G. The configuration 40G includes a PED holder assembly 10G, which in some embodiments is configured the same as the PED holder assembly 10D shown in FIG. 6 and be operatively connectable to the power and/or data output 56 through the cable assembly 58G and to the assistance request hub 54 through a communication path that includes the cable assembly 58G, the bed 42, and the assistance request communication cable assembly 44G. In an alternate embodiment, the PED holder assembly 10G includes a connection cable assembly 128 that operatively couples the PEG holder assembly 10G to a assistance request hub 54 and the power and/or data output 56.

Figure 10:
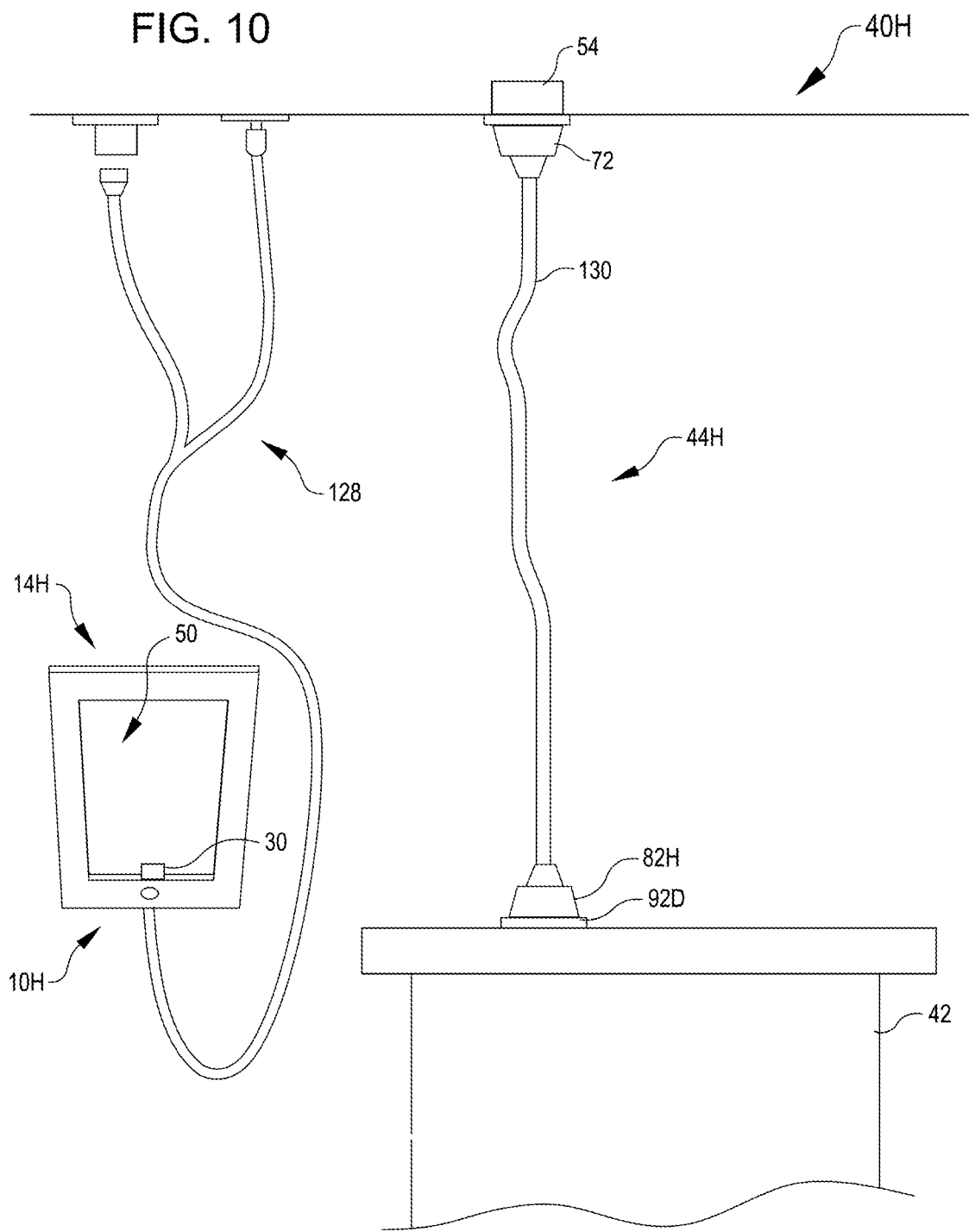
FIG. 10 shows a hospital room configuration that includes a PED holder assembly connected directly to a power and/or data device that supplies power and/or data to a PED, in accordance with embodiments, the PED holder assembly including a assistance request button.

FIG. 10 shows a hospital room configuration 40H that is similar to the hospital room configuration 40G shown in FIG. 9 except for differences described below. In the hospital room configuration 40H, the bed 42 is coupled to a assistance request hub 54 via a assistance request communication cable assembly 44H and a PED holder assembly 10H is coupled to a assistance request hub 54 and the power and/or data outlet 56 without being connected to the assistance request communication cable assembly 44H or the bed 42. The PED holder assembly 10H includes a PED holder 14H (which is configured similar to the PED holder 14D) and the connection cable assembly 128, which is connectable to each of a assistance request hub 54 and the power and/or data outlet 56 to operatively coupled the PED holder assembly 10H to the assistance request hub 54 and the power and/or data outlet 56. The hospital room configuration 40H can be implemented by adding the PED holder assembly 10H to an existing hospital room configuration that includes the bed 42 and the assistance request communication cable assembly 44H coupling the bed hub 92D to the assistance request hub 54. In the illustrated embodiment, the assistance request communication cable assembly 44H includes a single cable segment 130 that operatively connects the distal connector 82D to the proximal connector 72.

Figure 11:
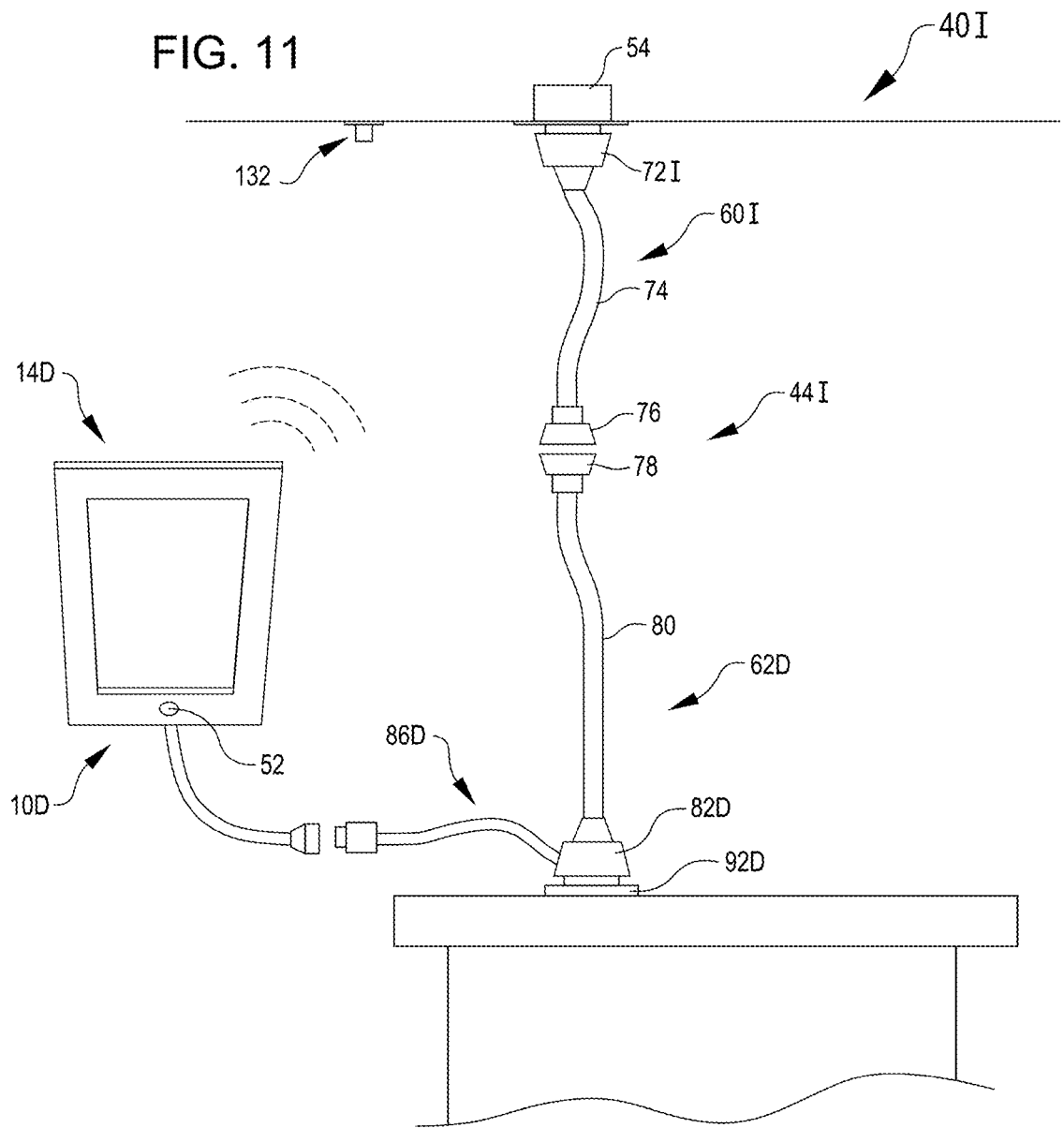
FIG. 11 shows a hospital room configuration in which a PED holder assembly is connected to a communication and power assembly for a patient bed, in accordance with embodiments, the PED holder assembly including a assistance request button and wireless communication functionality.

FIG. 11 shows a hospital room configuration 40i that is similar to the hospital room configuration 40E shown in FIG. 7 except for differences described below. The hospital room configuration 40i includes the PED holder assembly 10D and a assistance request communication cable assembly 44i. The assistance request communication cable assembly 44i is similar to the power and communication cable 44D shown in FIG. 6, but has a proximal cable assembly 60i that includes a proximal connector 72i that only connects to the assistance request hub 54 in contrast to the proximal connector 72 that connects to both the assistance request hub 54 and the power and/or data outlet 56 via the power and/or data cable assembly 58D as shown in FIG. 6. In the hospital room configuration 40i, the PED held by the PED holder 14D communicates wirelessly to a wireless router 132. The PED holder 14D can include a rechargeable battery that supplies power to recharge and/or operate the PED. In some embodiments, the PED holder assembly 10D supplies the PED with power transferred to the PED holder assembly 10D by the assistance request communication cable assembly 44i.

Figure 12:
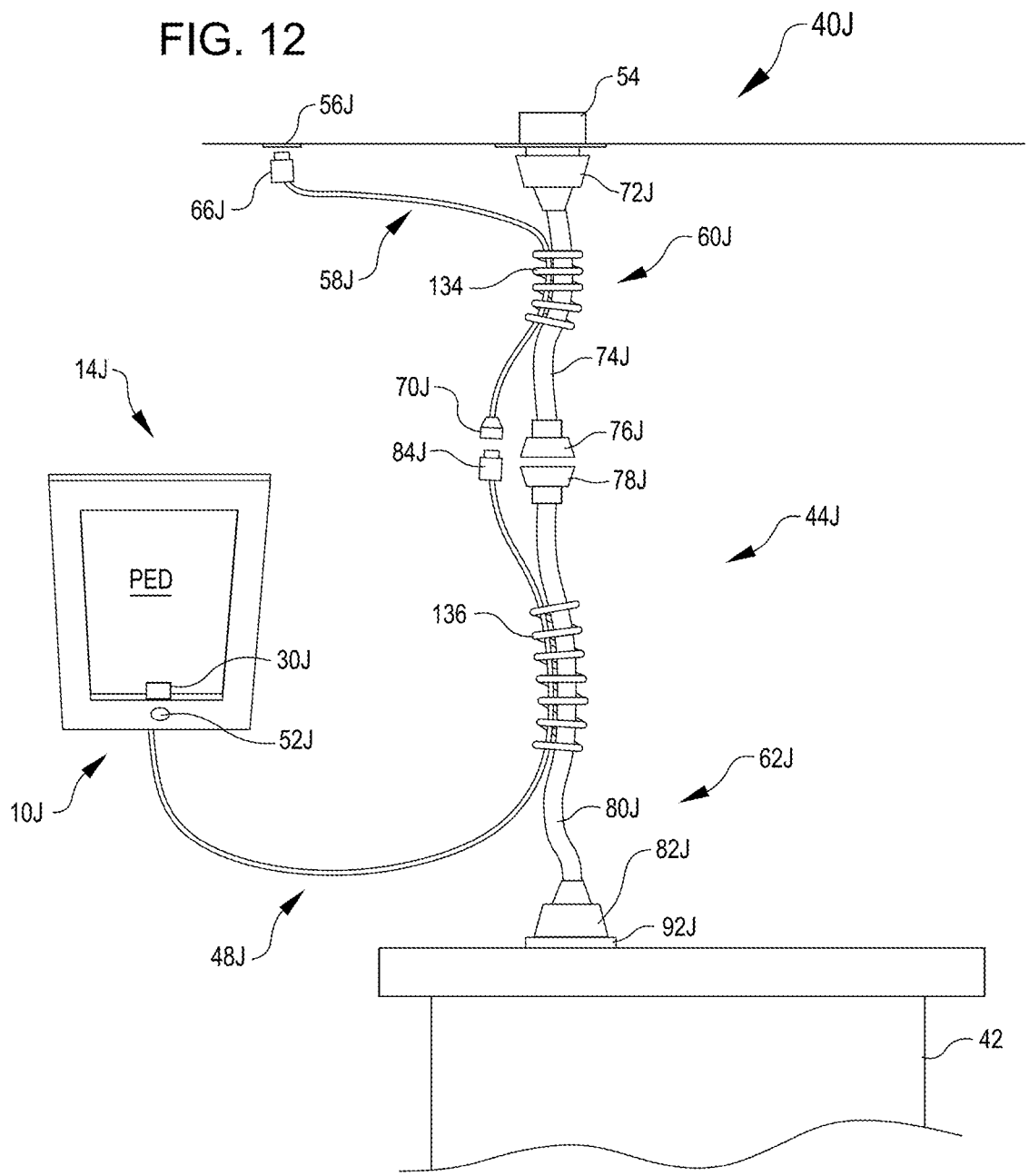
FIG. 12 shows a hospital room configuration that includes a PED holder assembly connected directly to a power and/or data device that supplies power and/or data to a PED, in accordance with embodiments, the PED holder assembly including a assistance request button and a connector disposed adjacent to a connector of a communication and power assembly for a patient bed.

FIG. 12 shows a hospital room configuration 40J that includes a PED holder assembly 10J, a power and data cable assembly 58J, a bed 42, and a assistance request communication cable assembly 44J. The PED holder assembly 10J includes a PED holder 14J and a power and data cable assembly 48J. The PED holder 14J includes a power and/or data output connector 30J for fitting into an input port 32 of a PED held by the PED holder 14J. The PED holder 14J further includes a assistance request button 52J that is operatively coupled to the connector 30J. The PED power and/or data cable assembly 58J includes a proximal connector 66J, a power and/or data cable 68J, and a distal connector 70J. The assistance request button 52J can be pressed to communicate a request for assistance to the PED held by the PED holder 30J. The power and data cable assembly 48J includes a proximal connector 84J that is connectable to the distal connector 70J to operatively connect the power and data cable assembly 48J to the outlet 56. The power and data cable assembly 48J operatively connects the power and/or data output connector 30 to a power and data outlet 56J via the power and data cable assembly 58J. In some embodiments, the PED held by the PED holder 14J, in response to receiving a request for assistance generated via pushing of the assistance request button 52J, transmits a request for assistance to an attendant station via the power and data outlet 56J. The assistance request communication cable assembly 44J includes a proximal cable assembly 60J and a distal cable assembly 62J. The proximal cable assembly 60J includes a proximal connector 72J, a communication cable 74J, and a distal connector 76J. The distal cable assembly 62J includes a proximal connector 78J, a communication cable 80J, and a distal connector 82J. The proximal connector 72J of the cable assembly 60J is connectable to the assistance request hub 54 to operatively connect the assistance request communication cable assembly 44J to the assistance request communication system. The proximal connector 78J of the cable assembly 62J is connectable to the distal connector 76J of the cable assembly 60J to operatively connect the cable assembly 62J to the assistance request communication system. The distal connector 82J of the cable assembly 62J is connectable to a bed connector 92J to operatively couple the bed 42 to the assistance request communication system.

In the illustrated embodiment, the distal cable assembly 62J is configured for quick disconnection from the proximal cable assembly 60J, and the power and data cable assembly 48J is configured for quick disconnection from the power and data cable assembly 58J, when the bed 42 needs to be moved. For example, the distal connector 76J and the proximal connector 78J can form a releasable magnetic connection, such as the magnetic connector disclosed in U.S. Pat. No. 9,147,965. As another example, the proximal connector 84J and the distal connector 70J can form a releasable magnetic connection, such as the magnetic connector disclosed in U.S. Pat. No. 9,147,965. In the illustrated embodiment, the proximal cable assembly 60J is coupled with the power and data cable assembly 58J via a proximal coupler 134, and the distal cable assembly 62J is coupled with the power and data cable assembly 48J via a distal coupler 136 so that the connectors 70J, 74J, 76J, 84J are held in close proximity to support quick disconnection of both connector 84J from connector 70J and connector 78J from connector 76J.

Figure 13:
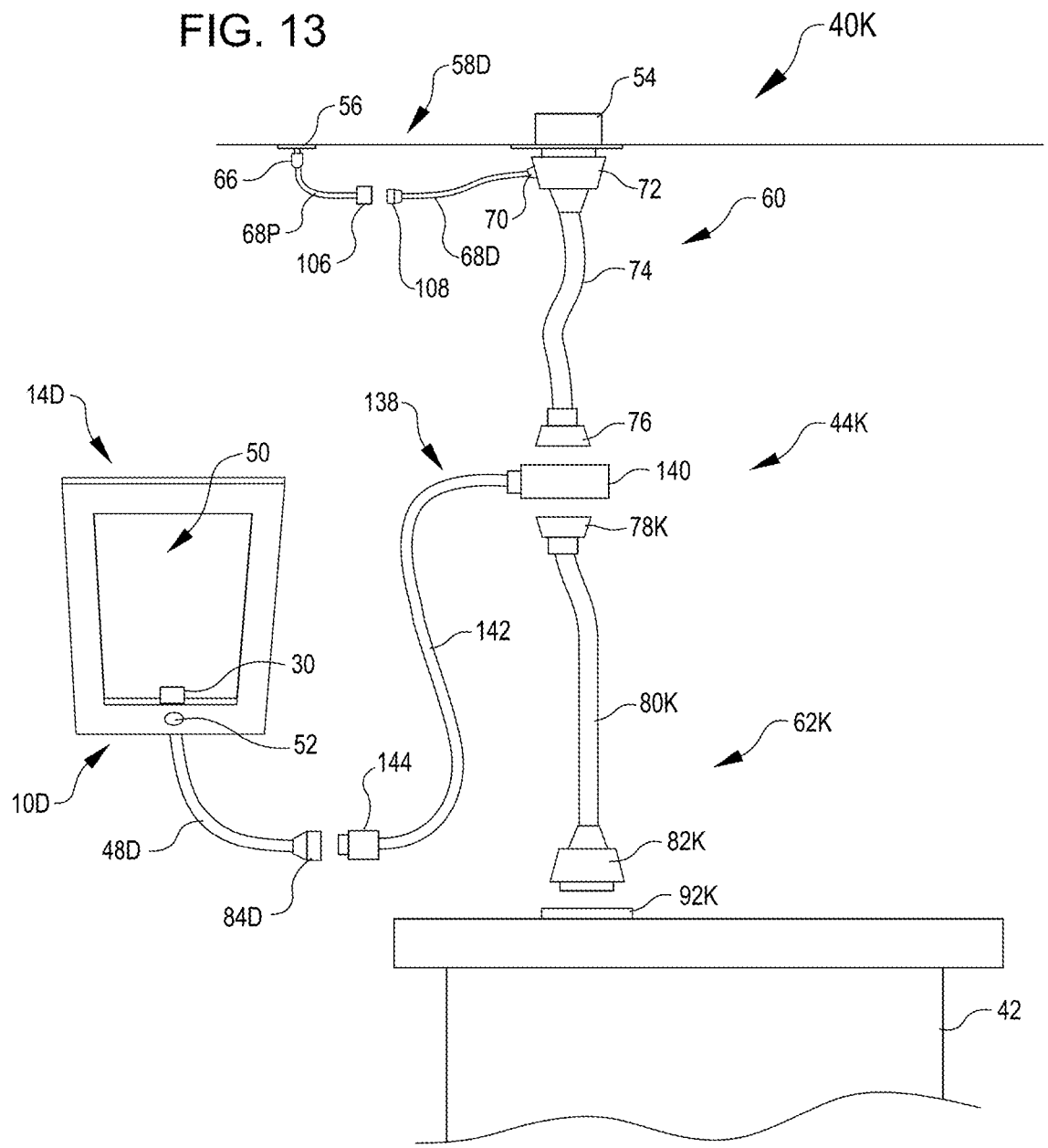
FIG. 13 shows a hospital room configuration in which a PED holder assembly is connected to a communication and power assembly for a patient bed, in accordance with embodiments, the PED holder assembly including a assistance request button.

FIG. 13 shows a hospital room configuration 40K that includes a hospital bed 42, a communication and power assembly 44K for the hospital bed 42, and the PED holder assembly 10D. The communication and power assembly 44K is configured similar to the communication and power assembly 44C, but including an intermediate coupler assembly 138. Reference identifiers associated with components of the communication and power assembly 44C that are the same or similar to components of the communication and power assembly 44K are the same or similar to reference identifiers associated with the components of the communication and power assembly 44K. The PED holder assembly 10D includes the proximal connector 84D, the cable assembly 48D, and the PED holder 14D. The PED holder 14D includes the power and/or data output connector 30 for fitting into an input port 32 of a PED held by the PED holder 14D. In the illustrated embodiment, the PED holder 14D includes a single assistance request button 52.

The communication and power assembly 44K operatively connects the PED holder assembly 10D to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder 14D through the communication and power assembly 44K. The communication and power assembly 44K includes the PED power and/or data cable assembly 58D, the proximal cable assembly 60, and a distal cable assembly 62K. The distal cable assembly 62k includes a proximal connector 78K, a assistance request communication cable 80K, and a distal connector 82K. The PED power and/or data cable assembly 58D includes the proximal connector 66, a proximal cable 68P, a connector 106, a connector 108, a distal cable 68D, and the distal connector 70. The proximal connector 66 is connectable to the outlet 56; the connector 108 is connectable to the connector 106; and the distal connector 70 is connectable to the proximal connector 72 of the cable assembly 60 to operatively connect the communication and power assembly 44K to the power and/or data outlet 56. The proximal connector 72 of the cable assembly 60 is connectable to the hub 54 to operatively connect the communication and power assembly 44K to the assistance request communication system. The proximal connector 78K of the cable assembly 62K is indirectly connectable, via the intermediate coupler assembly 138, to the distal connector 76 of the cable assembly 60 to operatively connect the cable assembly 62K to the assistance request communication system and, in some embodiments, to the outlet 56. The bed 42 includes a bed hub 92K to which the distal connector 82K is connectable to operatively connect the bed hub 92K to the assistance request communication system and, in some embodiments, to the outlet 56. In some embodiments, the bed 42 includes any suitable number of assistance request buttons 52 that are operatively coupled with the assistance request communication system via the bed hub 92K.

The intermediate coupler assembly 138 operatively connects the PED holder assembly 10D to the communication and power assembly 44K. The intermediate coupler assembly 138 includes a coupler 140, a cable 142, and a distal connector 144 operatively connected to the cable 142. The cable 142 is operatively connected to the coupler 140 and extends from the connector coupler 140. The coupler 140 is connectable to and between the distal connector 76 and the proximal connector 78K to operatively couple the cable assembly 62K and the intermediate coupler assembly 138 to the cable assembly 60 and, thereby, to the assistance request communication system and the outlet 56. The proximal connector 84D is connectable to the distal connector 144 to operatively coupled the PED holder assembly 10D to the communication and power assembly 44K and, thereby, to the assistance request communication system and the power and/or data outlet 56.

The hospital room configuration 40K can include any suitable number of quick disconnection features that enhance the ability to move the bed 42 and/or the PED holder assembly 10D. For example, in some embodiments, the distal connector 76 and the coupler 140 form a quick release connection, such as the magnetic connector disclosed in U.S. Pat. No. 9,147,965. In some embodiments, the coupler 140 and the proximal connector 78K form a quick release connection, such as the magnetic connector disclosed in U.S. Pat. No. 9,147,965. In some embodiments, the distal connector 144 and the proximal connector 84D form a quick release connection, such as the magnetic connector disclosed in U.S. Pat. No. 9,147,965.

Figure 14:
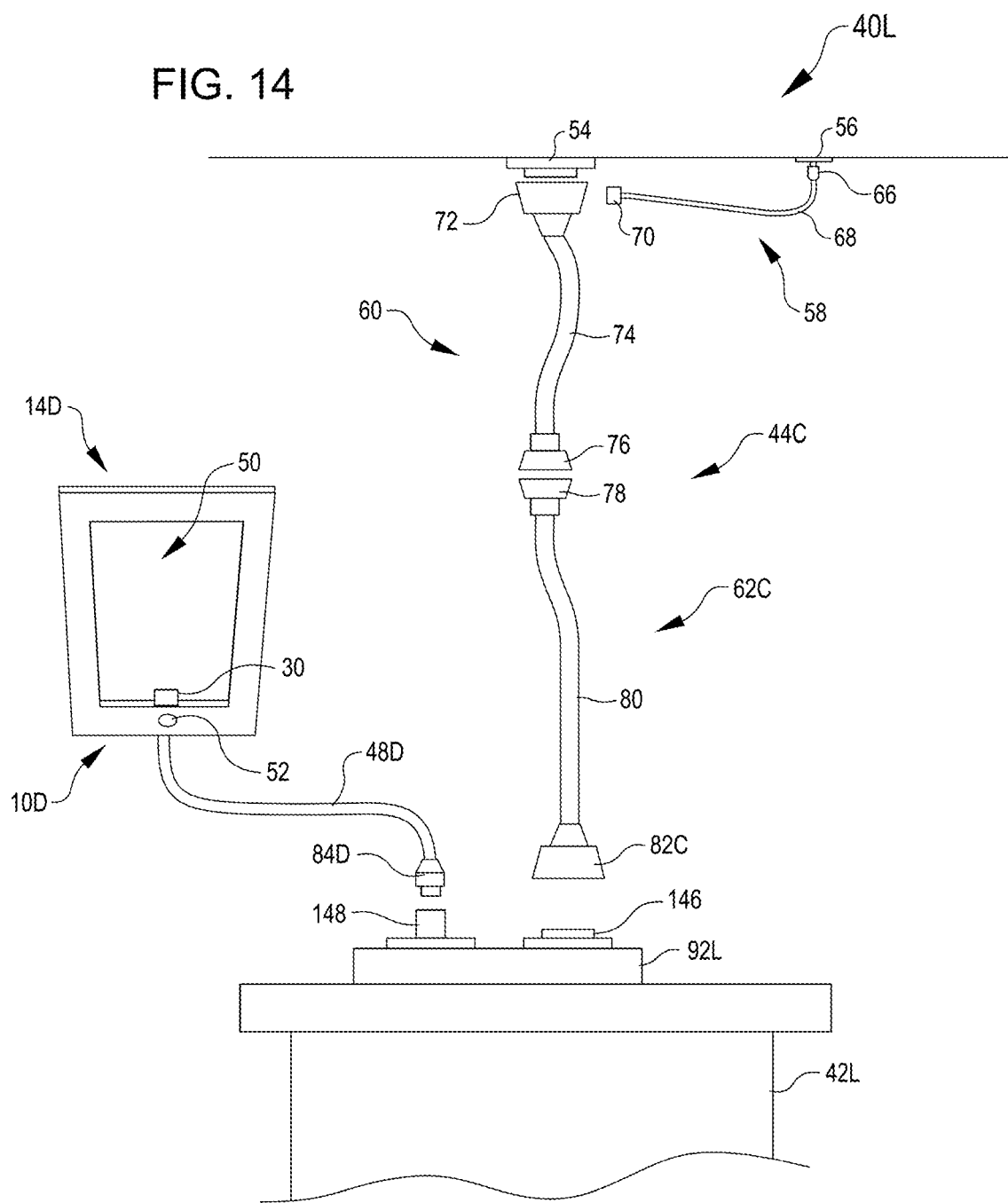
FIG. 14 shows a hospital room configuration in which a PED holder assembly is connected to a communication and power assembly for a patient bed, in accordance with embodiments, the PED holder assembly including a assistance request button.

FIG. 14 shows a hospital room configuration 40L that includes a hospital bed 42L, the communication and power assembly 44C, the PED holder assembly 10D. The bed 42L includes a bed hub 92L that includes a connector 146 and a connector 148. The distal connector 82C is connectable to the connector 146 to operatively connect the bed hub 92L to the assistance request communication system and the outlet 56. In some embodiments, the bed 42L includes any suitable number of assistance request buttons 52 that are operatively coupled with the assistance request communication system via the connector 146. The proximal connector 84D is connectable to the connector 148 to operatively connect the PED holder assembly 10D to the bed hub 92L and, thereby, to the assistance request communication system and the outlet 56 via the communication and power assembly 44C.

The hospital room configuration 40K can include any suitable number of quick disconnection features that enhance the ability to move the bed 42 and/or the PED holder assembly 10D. For example, in some embodiments, the distal connector 76 and the proximal connector 78 form a quick release connection, such as the magnetic connector disclosed in U.S. Pat. No. 9,147,965. In some embodiments, the distal connector 82C and the bed hub connector 146 form a quick release connection, such as the magnetic connector disclosed in U.S. Pat. No. 9,147,965. In some embodiments, the bed hub connector 148 and the proximal connector 84D form a quick release connection, such as the magnetic connector disclosed in U.S. Pat. No. 9,147,965.

Figure 15:
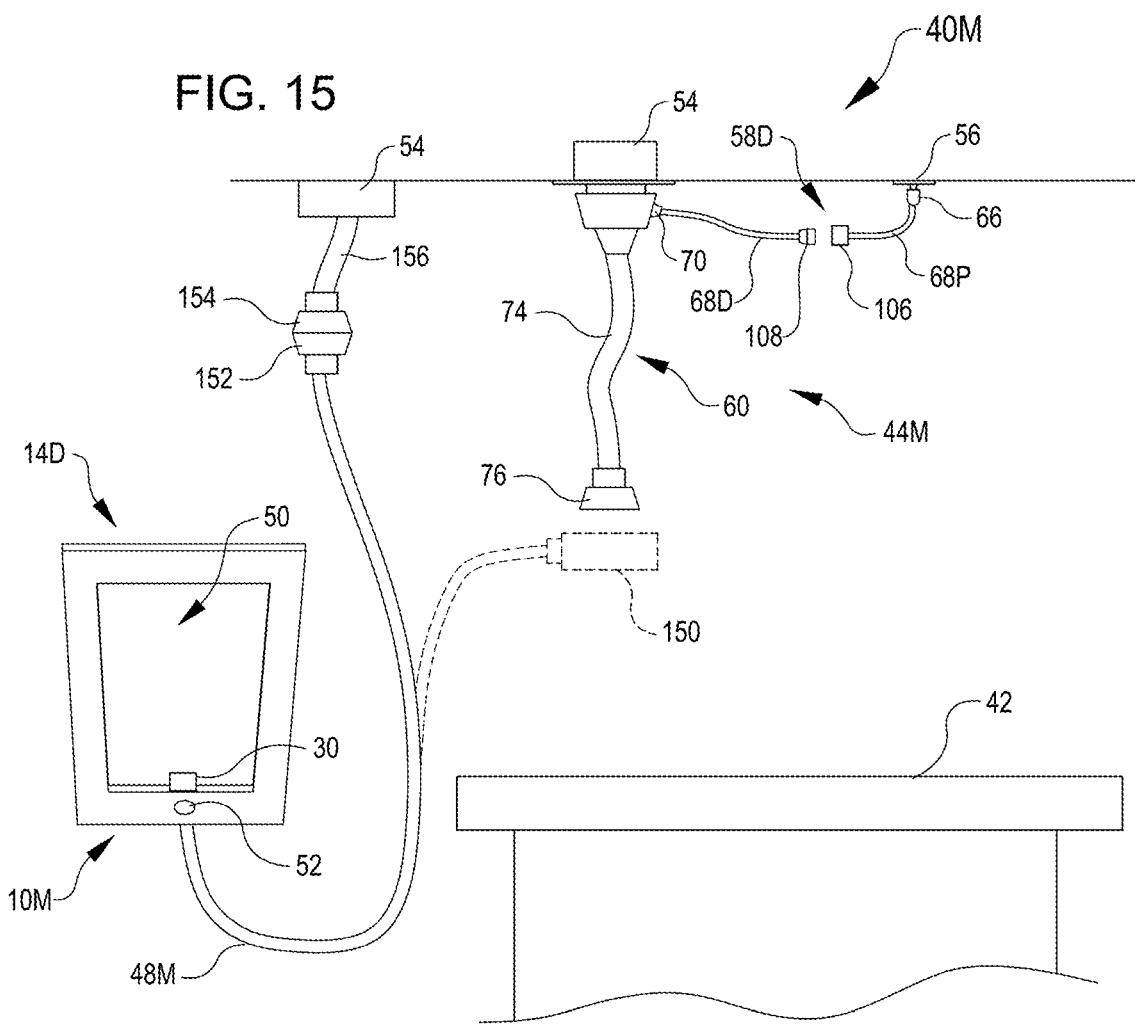
FIG. 15 shows a hospital room configuration that includes a PED holder assembly that can be connected to a communication and power assembly for a patient bed or connected directly to a power and/or data device that supplies power and/or data to a PED, in accordance with embodiments, the PED holder assembly including a assistance request button.

FIG. 15 shows a hospital room configuration 40M that includes a hospital bed 42, a communication and power assembly 44M, and a PED holder assembly 10M. The communication and power assembly 44M includes the PED power and/or data cable assembly 58D and the proximal cable assembly 60. The PED holder assembly 10M is configured similar to the PED holder assembly 10D. The PED holder assembly 10M includes the PED holder 14D, a power and communication cable 48M, and a proximal connector. In some embodiments, the proximal connector of the PED holder assembly 10M is a proximal coupler 150. The proximal coupler 150 is connectable to the distal connector 76 to operatively couple the PED holder 14D to the assistance request hub 54 and the power and/or data outlet 56 via the power and communication cable 48M. In some embodiments, the proximal connector of the PED holder assembly 10M is a proximal connector 152. The proximal connector 152 is connectable to a distal connector 154 to operatively couple the assistance request button 52 of the PED holder assembly 10M to a assistance request hub 54 via a connection cable 156. In some embodiments, the assistance request hub 54 supplies power to the PED holder 14D via a power transmission path including the connection cable 156, the distal connector 154, the proximal connector 152, the power and communication cable 48M, and the power and/or data output connector 30.

The hospital room configuration 40M can include any suitable number of quick connection features for operatively coupling the PED holder assembly 10M to a assistance request hub 54 or to both a assistance request hub 54 and a power and/or data outlet 56. For example, in some embodiments, the distal connector 76 and the proximal coupler 150 form a quick release connection, such as the magnetic connector disclosed in U.S. Pat. No. 9,147,965. In some embodiments, the distal connector 154 and the proximal connector 152 form a quick release connection, such as the magnetic connector disclosed in U.S. Pat. No. 9,147,965.

Figure 16:
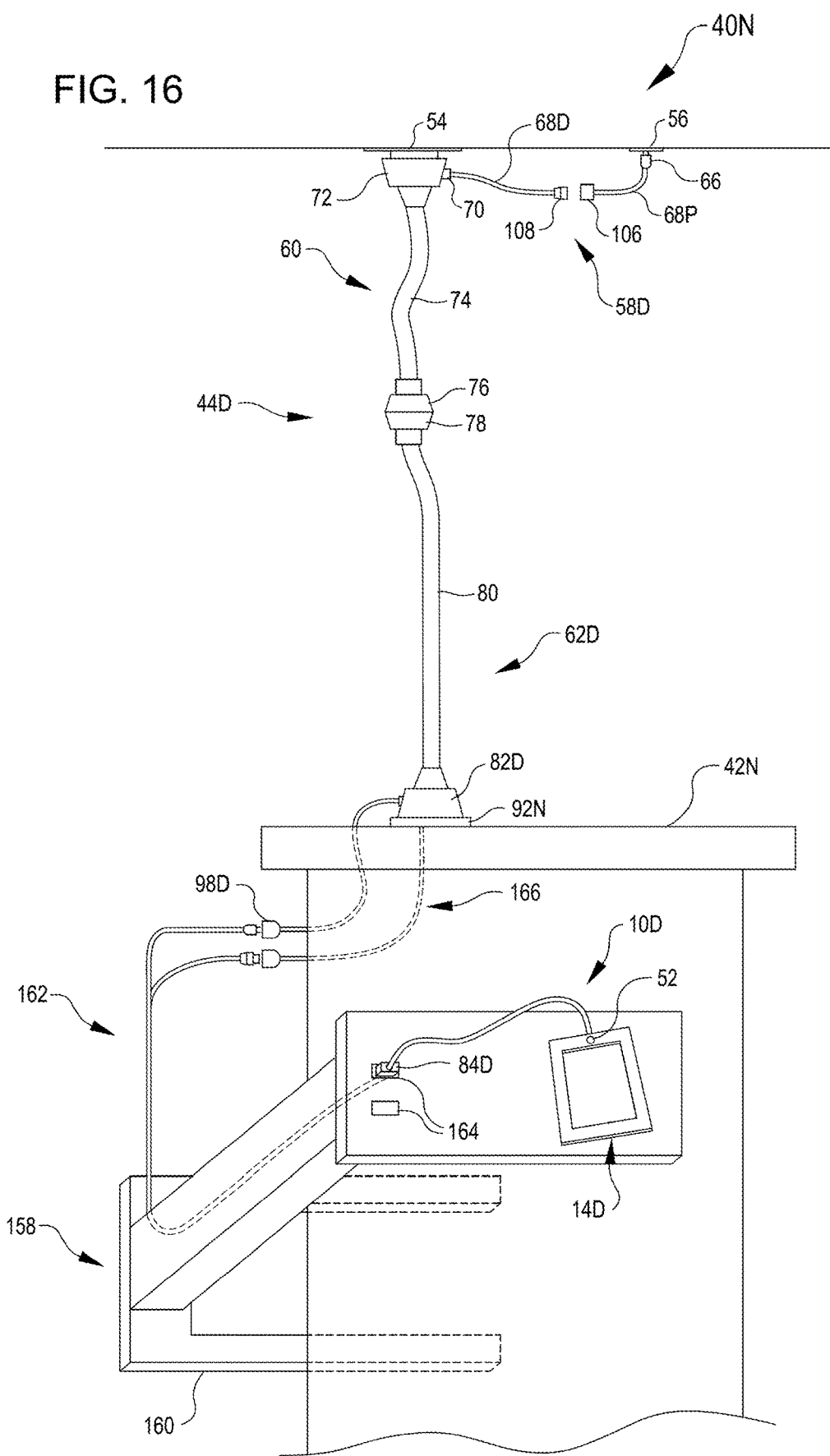
FIG. 16 shows a hospital room configuration in which a PED holder assembly is connected to a bed stand assembly connected to a communication and power assembly for a patient bed, in accordance with embodiments, the PED holder assembly including a assistance request button.

FIG. 16 shows a hospital room configuration 40M that includes a hospital bed 42N, the communication and power assembly 44D, the PED holder assembly 10D, and a bed stand assembly 158. The communication and power assembly 44D includes the PED power and/or data cable assembly 58D, the proximal cable assembly 60, and the distal cable assembly 62D. The bed 42N includes a bed hub 92N to which the distal connector 82D can be coupled to operatively couple the bed hub 92N to the assistance request hub 54 and the power and/or data outlet 56 via the communication and power assembly 44D.

The bed stand assembly 158 includes a bed stand 160, a connection cable assembly 162, and connection ports 164 mounted to the bed stand 160. The connection cable assembly 162 operatively couples each of the connection ports to both the bed hub 92N and the distal cable assembly 62D. In the illustrated embodiment, the connection cable assembly 162 is connectable to the bed hub 92N via a connection cable 166 to operatively couple each of the connection ports 164 to the assistance request hub 54 via the communication and power assembly 44D. Also in the illustrated embodiment, the connection cable assembly 162 is connectable to the distal connector 98D of the distal cable assembly 62D to operatively couple each of the connection ports 164 to the power and/or data outlet 56 via the communication and power assembly 44D. The proximal connector 84D of the PED holder assembly 10D is connectable to any one of the connection ports 164 to operatively couple the PED holder 14D to the assistance request hub 54 and the power and/or data outlet 56.

The hospital room configuration 40N can include any suitable number of quick disconnection features that enhance the ability to move the bed 42 and/or the bed stand assembly 158. For example, in some embodiments, the distal connector 76 and the proximal connector 78 form a quick release connection, such as the magnetic connector disclosed in U.S. Pat. No. 9,147,965.

Figure 17:
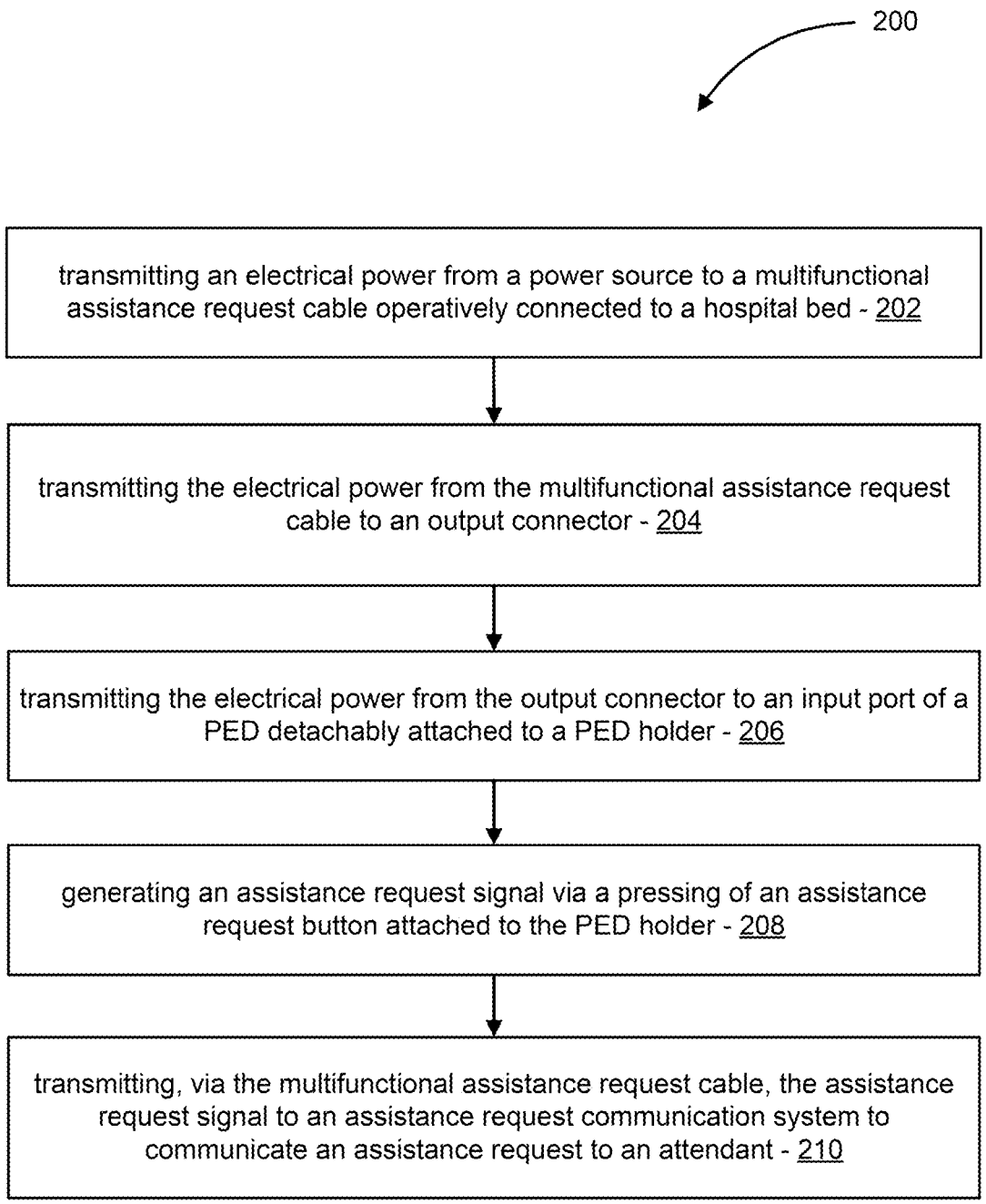
FIG. 17 is a simplified schematic diagram of a method of transmitting power to a portable electronic device (PED) over a multifunctional assistance request cable and a request for assistance signal over the multifunctional assistance request cable, in accordance with embodiments.

FIG. 17 is a simplified schematic diagram of a method 200 of transmitting power to a portable electronic device (PED) over a multifunctional assistance request cable and a request for assistance signal over the multifunctional assistance request cable, in accordance with embodiments. Any suitable assemblies, such as assemblies described herein, can be used to practice the method 200. The method 200 includes transmitting an electrical power from a power source to a multifunctional assistance request cable operatively connected to a hospital bed (act 202), transmitting the electrical power from the multifunctional assistance request cable to an output connector (act 204), transmitting the electrical power from the output connector to an input port of a PED detachably attached to a PED holder (act 206), generating an assistance request signal via a pressing of an assistance request button attached to the PED holder assembly (act 208), and transmitting, via the multifunctional assistance request cable, the assistance request signal to an assistance request communication system to communicate an assistance request to an attendant (act 210). Acts 202-210 can be accomplished using any suitable approach, such as the approaches described herein.

Figure 18:
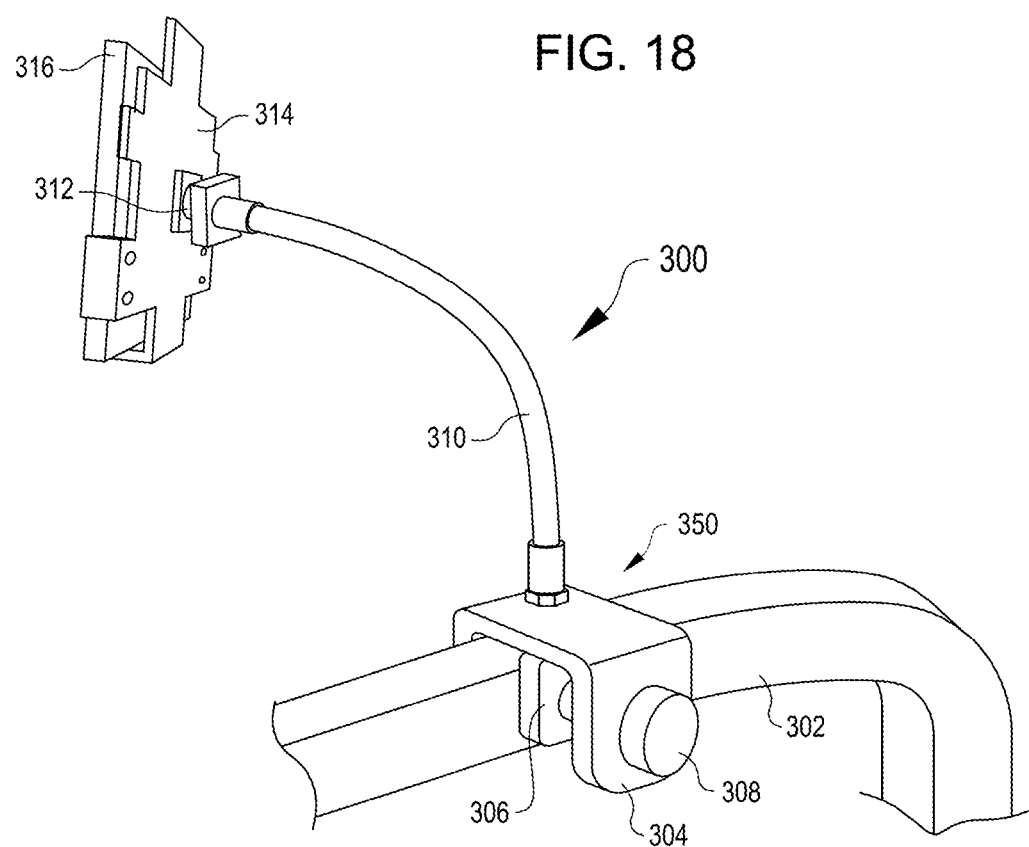
FIG. 18 shows a PED connected to a rail using a PED holder with a clamp, in accordance with some embodiments.

FIG. 18 shows a PED 316 connected to a rail 302 using a PED holder 300 with a clamp 350, in accordance with some embodiments. The PED holder 300 includes the clamp 350, a positionable arm 310, and a PED holder device 314. The PED holder device 314 may include an enclosure that retains a PED, such as depicted in FIG. 2. The PED 316 may be powered through a power and data cable that is routed through the positionable arm 310 such that data and power are provided to the PED 316 while in the PED holder 300. The power and data cable may also enable an assistance request or other input button or device connected to the PED holder device 314 to provide a signal over the power and data cable. The PED holder device 314 is coupled to the positionable arm 310 with a ball joint 312 such that the PED or positionable by adjusting the positionable arm 310 in any possible orientation and further positionable by adjusting a rotation, in at least one direction, of the PED 316 at the ball joint 312. The positionable arm 310 may be any suitable positionable device such as a flexible member having a rigid core, or other such device capable of being positioned and remain in the position without additional external force. The positionable arm 310 may have a channel or path along which the data and power may be provided to the PED 316. The channel may be through a center of the positionable arm 310 or along an edge or adjacent the same. The channel may include a series of clamps or fixtures arranged along the length of the positionable arm for retaining cables, such as a power and data cable.

In some examples, power may be provided to the PED 316 as well as to an additional device of the PED holder 300. In some examples, a power cord (not shown) may provide power to the PED holder 300 from a power source, such as an outlet. The power may be provided at one hundred and twenty volts, twelve volts, or five volts. In some examples, the power may arrive at the PED holder 300 and subsequently be routed through a power adapter built in to the PED holder to provide twelve or five volt power to peripheral devices. In some examples an outlet may be provided on the PED holder 300, for example on the clamp 350, through which additional devices may be charged.

In some examples, the PED holder 300 may be configured to attach to a side rail 302 of a patient bed in a health care facility. In some examples, the PED holder 300 may be configured to connect to various rails, devices, and surfaces, including those having regular geometric cross-sections as well as irregular geometric cross sections. The PED holder 300 may also be configured to connect to an edge of a panel. The clamp 350, as shown and described in FIGS. 19-20, may clamp to rails, rods, panels, and various devices having parallel surfaces, having round sides, having irregular geometry, having non-parallel sides, and any other geometry. This is accomplished and enabled by the shape and flexibility in the clamping angles of the surfaces of clamp 350.

The clamp 350 includes a first clamp surface 306 actuated by actuation member 308 to adjust the positioning of the first clamp surface 306. By actuating the actuation member 308, the first clamp surface 306 can apply pressure to the first side rail 302 to secure the PED holder 300 to the first side rail 302. Body 304 provides connection between actuation device 308, a second clamping surface, and positionable arm 310.

Figure 19:
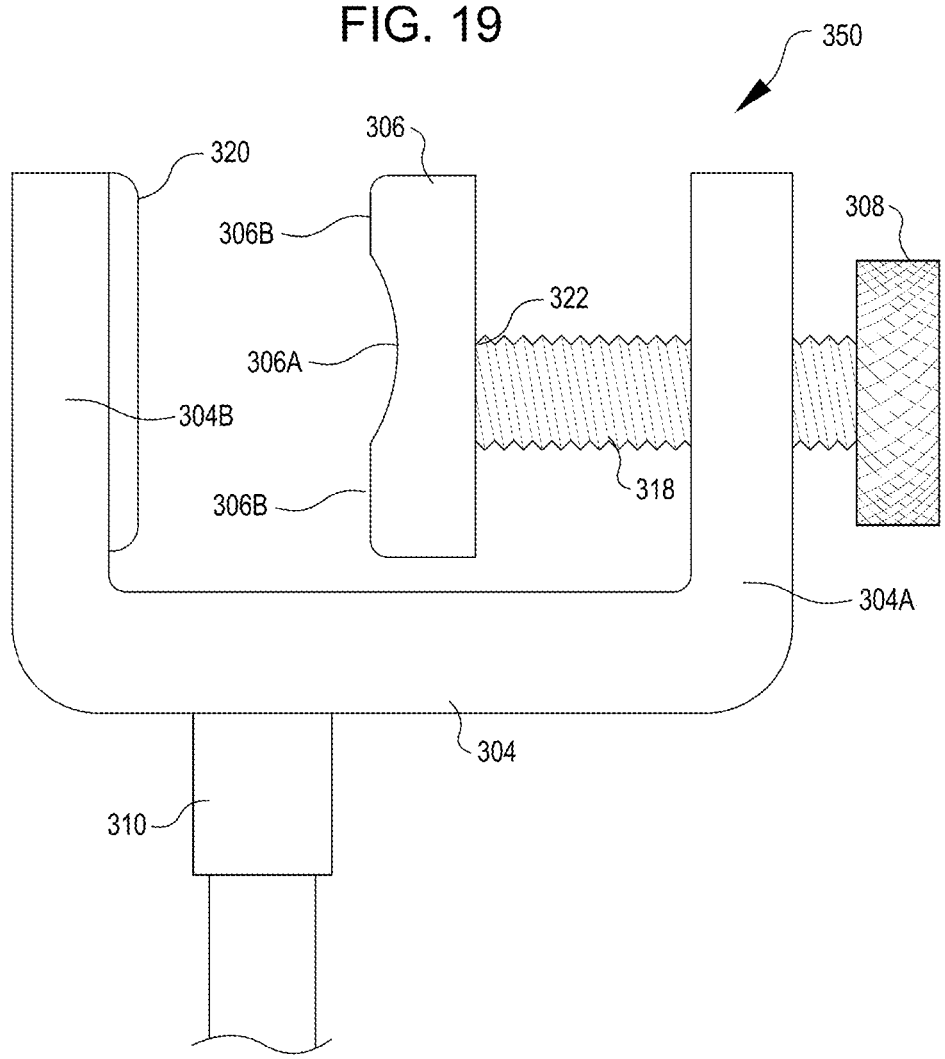
FIG. 19 shows a detail view of the clamp of the PED holder of FIG. 18, in accordance with some embodiments.

FIG. 19 shows a detail view of the clamp 350 of the PED holder 300 of FIG. 18, in accordance with some embodiments. The clamp 350 includes a first clamp surface 306, a second clamp surface 320, actuation device 308, and body 304. In particular, the first clamp surface 306 is positionable by actuating the actuation device 308, thereby adjusting a relative position of the first clamp surface 306 and the second clamp surface 320.

The body 304 is shown having a U-shape with a first extension 304A and a second extension 304B providing parallel, or near parallel surfaces for use in applying a clamping force. The first extension 304A and the second extension 304B may be positioned at varying angles and varying distances. In some examples, the first extension 304A and the second extension 304B are separated by a distance of less than three inches. In some examples, the distance is greater than three inches, less than four inches, or any suitable distance to ensure the first clamp surface 306 and the second clamp surface 320 can fit around intended devices, rails, and surfaces.

In some examples, the body 304 may include a power conversion device, such that input power provided to the power converter is different from output power supplied from the power converter to a device electrically coupled to the converter, such as through an interface of the PED holder 300. The power conversion device may output a power supply at a range of 0.5 to 2 Watts, or more, and be supplied with a different power supply, such as a greater wattage or different voltage of power supply.

The actuation device 308 is shown with threads 318 interacting with body 304 at the first extension 304A. The threads 318 thread through the first extension 304A such that rotation of the actuation device 308 causes the first clamp surface 306 to advance or retreat along a movement axis that intersects the first clamp surface 306 and the second clamp surface 320. The movement axis may be aligned with the actuation device 308 such that actuation of the actuation device results in movement of the first surface along the direction of the movement axis. The actuation device 308 is shown as a threaded rod to advance and position the first clamp surface 306, however in some examples other actuation devices such as cam devices, levers, ratchet devices, and other such actuation devices, including linear actuation devices that are able to resist an applied force and be releasably secured may be substituted. The actuation device may be able to position the first clamp surface over a range of up to three inches, or greater, based on the distance between the first extension 304A and the second extension 304B.

In some instances, the actuation device 308 may include a locking element to prevent accidental or unintentional release of the actuation device 308 while in use. Examples of locking devices may include locking pins, set screw-type locks, ball detente devices, and other such devices that may be used to resist rotation or actuation of the actuation device 308 unless intended.

The threads 318 of the actuation device meet the first clamp surface 306 at a joint 322. The joint 322 may be a ball joint or other such joint that enables or allows the actuation device 308 to rotate without requiring rotation of the first clamp surface 306. The first clamp surface may additionally be limited in rotation by interference between the first clamp surface 306 and the body 304. The limited rotation may be less than one hundred and eighty degrees, less than ninety degrees, less than forty-five degrees, or any other limited range of rotation. For example, the first clamp surface 306 may be part of a rectangular surface that collides with body 304 after rotation of less than thirty degrees and thereby prevents full rotation of the first clamp surface 306. The limited rotation of the first clamp surface 306 may aid with alignment of features of the first and/or second clamp surfaces 306 and 320 with rails or surfaces of health care facility equipment. In some examples, the first clamp surface may be free to rotate to accommodate additional geometry of rails, but may require manual alignment of features on the first clamp surface 306.

The first clamp surface 306 and the second clamp surface 320 may each be formed of a plastic, rubber, metal, cork, or any other such rigid or semi-rigid material. Use of a semi-rigid material may enable additional friction and grip, particularly on rounded metallic rails, such as IV stands and the like. In some examples the first clamp surface 306 and the second clamp surface 320 may have a Shore A durometer of between twenty and sixty. In some examples the durometer rating may be less than twenty or greater than sixty.

The first clamp surface 306 is shown having different regions of different shapes, for example to accommodate rails having rounded profiles. The profile shown includes a first and second flat portion 306B that extend the length of the first clamp surface 306. The first clamp surface 306 may also include a curved portion 306A to interface with surfaces of rails, especially of non-rectangular rails. The first clamp surface 306 is shown with the first and second flat portions 306B and the concave curved portion 306A. In some examples the curved portion may have a radius of curvature of greater than two inches. In some examples, the radius of curvature may be less than two inches. The concave curved portion 306A enables the clamp 350 to engage with rounded rails by providing engagement around greater surface area of the rail. In instances where the first clamp surface 306 is flat, clamping against a round rail may result in only a thin line of contact with the rail, and rotation of the clamp 350 relative to the rail is possible. With the concave curved portion 306A, rotation of the clamp 350 relative to the rail is minimized and prevented because of the geometry of the concave surface that interacts with the rail.

In some examples, the first clamp surface 306 may include additional concave portions or may include convex portions in place of or in addition to the concave portion shown in FIG. 19. A convex portion on the first clamp surface may, for example, provide greater engagement with a rail having a concave surface. The second clamp surface 320 may, similar to the first clamp surface 306, include flat, convex, and/or concave portions.

Figure 20:
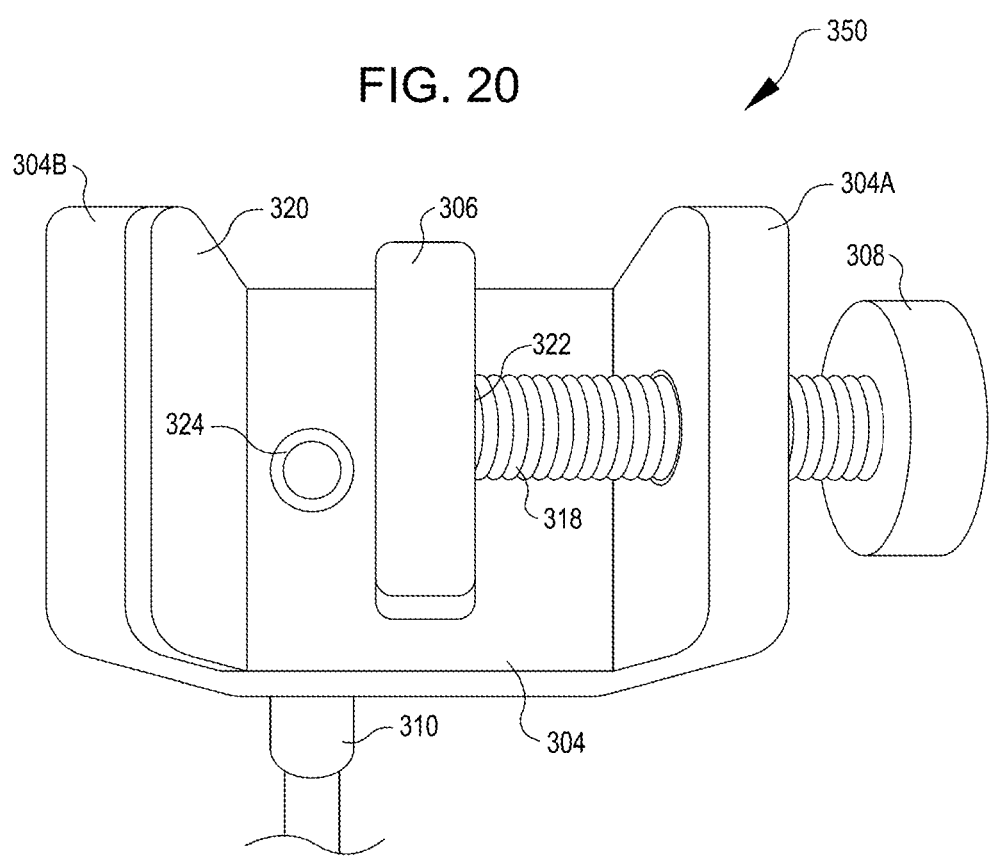
FIG. 20 shows a second detail view of the clamp of the PED holder of FIG. 19, in accordance with some embodiments.

FIG. 20 shows a second detail view of the clamp 350 of the PED holder 300 of FIG. 19, in accordance with some embodiments. The body 304 is shown with positionable arm 310 connected to the body 304 between the first extension 304A and the second extension 304B. The positionable arm 310 defines a channel 324 which serves as a passageway through which a data and power cable may be routed to provide a power and data connection to the PED 316. In some examples the positionable arm 310 may be connected to one end of the body 304, such as to second extension 304B.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A portable electronic device (PED) holder assembly for use in a health care facility, comprising:
   a device for connecting to health care facility equipment, the device comprising:
     a body having a "U"-shape comprising a base member with a first extension and a second extension extending perpendicularly from opposite ends of the base member;
     a first surface for positioning against a first side of the health care facility equipment, the first surface coupled to the first extension; and
     a second surface coupled to the second extension and for positioning against a second side, opposite the first side, when the device is installed on the health care facility equipment, the first surface or second surface positionable along a movement axis extending from the first extension to the second extension in (1) an open position where the first surface and second surface are released to permit installation of the device on the health care facility equipment and a (2) closed position where the first surface and second surface are positioned against the first side and the second side of the health care facility equipment;
   a PED holder adapted to hold a PED;
   arm coupled to the device; and
   a power interface connected to a power supply of the health care facility for providing power to the PED or the PED holder.

2. The PED holder assembly of claim 1, wherein the PED holder comprises:
   one or more interfaces adapted for connection to a power and data cable of a health care facility, the one or more interfaces disposed in the PED holder; and
   an assistance request button associated with requesting assistance in the health care facility, the assistance request button disposed in the PED holder or the power and data cable, wherein
     a first interface of the one or more interfaces is operatively coupled with the PED such that power received from the power and data cable is provided from the first interface to the PED, and
     a second interface of one of the one or more interfaces is operatively coupled with a communication system of the health care facility such that an assistance request signal is provided from the second interface to the communication system via the power and data cable.

3. The PED holder assembly of claim 2, wherein the second interface comprises a releasable connector.

4. The PED holder assembly of claim 1, wherein the first surface is coupled to the first extension via an actuation member, the actuation member coupled to the first surface to enable rotation of the first surface through a limited range of rotation or tilt of less than one hundred and eighty degrees.

5. The PED holder assembly of claim 4, wherein rotation of the first surface is limited due to an interaction between the first surface and body.

6. The PED holder assembly of claim 1, wherein the arm comprises a plurality of clamps arranged along a length thereof to support a power or data cable connected to a system of the health care facility.

7. The PED holder assembly of claim 1, wherein the body comprises a power converter configured to receive power input from a power cable of a health care facility and output a power output at a different voltage from a voltage of the power input.

8. The PED holder assembly of claim 7, wherein the power converter receives the power input at twelve volts or greater and outputs the power output at less than twelve volts.

9. The PED holder assembly of claim 1, wherein the power interface comprises a power outlet connected to the power supply.

10. The PED holder assembly of claim 1, wherein the device comprises an actuation device that changes a distance between the first surface and the second surface between the open position and the closed position and apply a force against the health care facility equipment.

11. The PED holder assembly of claim 1, wherein each of the second surface and first surface comprise a planar surface to enable the device to secure against a planar surface of health care facility equipment.

12. The PED holder assembly of claim 1, wherein the device further comprises a security device to resist removal of the device from the first side.

13. The PED holder assembly of claim 1, wherein at least one of the first surface of the second surface comprises a curved surface.

14. The PED holder assembly of claim 13, wherein the curved surface comprises a concave surface.

15. The PED holder assembly of claim 13, wherein the curved surface comprises a convex surface.

16. The PED holder assembly of claim 1, wherein the first surface and the second surface are positionable with a separation of up to three inches, along the movement axis.

17. The PED holder assembly of claim 1, wherein the first surface and second, when in the closed position, comprise a geometry capable of securely clamping without rotation, against the first side.

18. A device for connecting to health care facility equipment, the device comprising:
   a body;
   a first surface for positioning against a first side of the health care facility equipment, the first surface comprising a concave surface;
   a second surface for positioning against a second side of the health care facility equipment, opposite the first side, when the device is installed on the health care facility equipment, the first surface or second surface positionable in (1) an open position where the first surface and the second surface are released to permit installation of the device and a (2) closed position where the first surface and second surface are positioned against the first side and the second side of the health care facility equipment;

an arm coupled to both the body and to an electronic device holder to enable positioning of the electronic device holder; and a power interface connected to a power supply of a health care facility for providing power to the electronic device holder or an electronic device disposed in the electronic device holder.

19. The device of claim 18, wherein the first surface is a planar surface opposite the second surface.

20. The device of claim 18, wherein the second surface and the first surface each comprise a compressible layer that deforms when the second surface and the first surface are positioned with a force against the first side and the second side.

21. The device of claim 20, wherein the compressible layer comprises a rubber having a hardness in a range of twenty Shore A to sixty Shore A durometer.

22. The device of claim 18, wherein the second surface comprises a concave portion opposite the concave portion of the first surface.

23. The device of claim 18, wherein the body comprises one or more interfaces adapted for connection to at least one of a power or a data cable of a health care facility, the one or more interfaces communicatively coupleable to the electronic device or the electronic device holder.

24. The device of claim 23, wherein the electronic device holder comprises power and data connections for coupling the power and data cable of the health care facility with the electronic device.

25. The device of claim 18, wherein the body comprises a power converter configured to receive power input from a power cable of a health care facility and output a power output at a different voltage from a voltage of the power input.

26. The device of claim 18, wherein the arm comprises a conduit for a power and data cable of the health care facility.

27. The device of claim 18, wherein the second surface is positionable in the open position and the closed position by actuating an actuation mechanism.

28. The device of claim 27, wherein the actuation mechanism comprises a threaded connection, a cam lever, or ratchet device.

* * * * *